(12) United States Patent
Merritt

(10) Patent No.: US 11,406,334 B2
(45) Date of Patent: Aug. 9, 2022

(54) INTRAVASCULAR DEVICE MOVEMENT SPEED GUIDANCE AND ASSOCIATED DEVICES, SYSTEMS, AND METHODS

(71) Applicant: KONINKLIJKE PHILIPS N.V., Eindhoven (NL)

(72) Inventor: Fergus Merritt, Gold River, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 336 days.

(21) Appl. No.: 16/542,001

(22) Filed: Aug. 15, 2019

(65) Prior Publication Data

US 2020/0069264 A1 Mar. 5, 2020

Related U.S. Application Data

(60) Provisional application No. 62/725,867, filed on Aug. 31, 2018.

(51) Int. Cl.
*A61B 6/12* (2006.01)
*A61B 8/12* (2006.01)
(Continued)

(52) U.S. Cl.
CPC .............. *A61B 6/12* (2013.01); *A61B 5/0215* (2013.01); *A61B 5/6851* (2013.01); *A61B 6/022* (2013.01);
(Continued)

(58) Field of Classification Search
CPC ........................................................ A61B 6/12
See application file for complete search history.

(56) References Cited

U.S. PATENT DOCUMENTS 9,216,065 B2 12/2015 Cohen
2002/0115931 A1 8/2002 Strauss
(Continued)

FOREIGN PATENT DOCUMENTS

WO 2016052289 A1 4/2016
WO WO-2017102340 A1 * 6/2017 ............. A61B 5/064

OTHER PUBLICATIONS

Wahle, Andreas et al "Geometrically Correct 3-D Reconstruction of Intravascular Ultrasound Images by Fusion with Biplane Angiography—Methods and Validation", IEEE Transactions on Medical Imaging, vol. 18, No. 8, Aug. 1999, pp. 686-699.

*Primary Examiner* — Colin T. Sakamoto

(57) ABSTRACT

In an embodiment, a medical system is disclosed. One embodiment of the medical system comprises a medical processing unit in communication with an intravascular instrument configured to be moved longitudinally within a body lumen and in further communication with a radiographic imaging source configured to obtain radiographic images of the intravascular instrument while the intravascular instrument is moved longitudinally within the body lumen. The medical processing unit is configured to receive radiographic images obtained by the radiographic imaging source, track the intravascular instrument within the radiographic images while the intravascular instrument is moved longitudinally within the body lumen, calculate a movement speed based on the tracking, compare the calculated movement speed to a predefined target movement speed, generate a speed-adjustment suggestion based on the comparison, and output the speed-adjustment suggestion to a display for review by a user.

20 Claims, 13 Drawing Sheets

(51) Int. Cl.
  *A61B 5/0215* (2006.01)
  *A61B 5/00* (2006.01)
  *A61B 6/00* (2006.01)
  *A61B 6/02* (2006.01)
  *A61M 25/01* (2006.01)

(52) U.S. Cl.
  CPC ............... *A61B 6/504* (2013.01); *A61B 8/12* (2013.01); *A61M 25/0108* (2013.01)

(56) References Cited

U.S. PATENT DOCUMENTS

| | | |
|---|---|---|
| 2010/0094127 A1* | 4/2010 | Xu ..................... A61B 5/7425 600/425 |
| 2010/0157041 A1 | 6/2010 | Klaiman |
| 2012/0029339 A1 | 2/2012 | Cohen |
| 2015/0080711 A1 | 3/2015 | Hendriks |
| 2016/0015327 A1 | 1/2016 | Merritt |
| 2016/0029999 A1 | 2/2016 | Corl |
| 2016/0073972 A1 | 3/2016 | Alpert |
| 2016/0374716 A1 | 12/2016 | Kessler |
| 2017/0065206 A1* | 3/2017 | Bozkaya ............... A61B 6/504 |

* cited by examiner

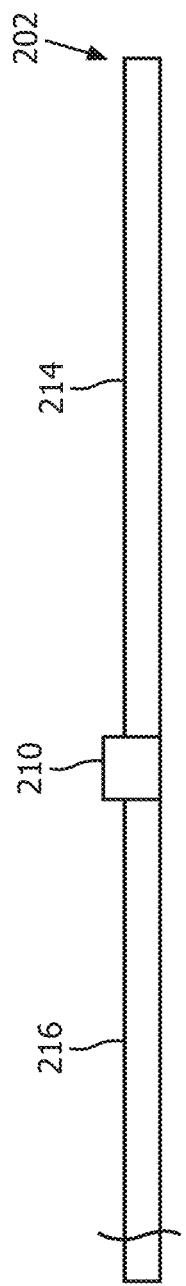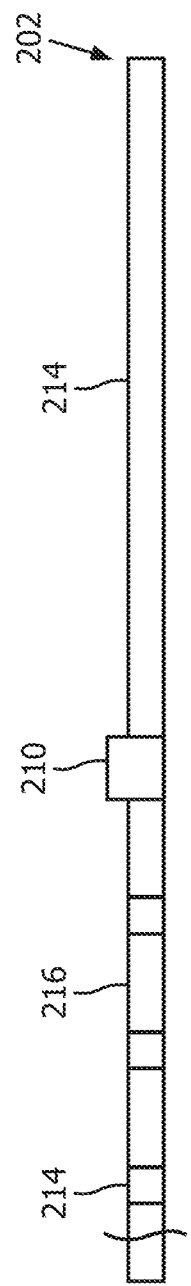

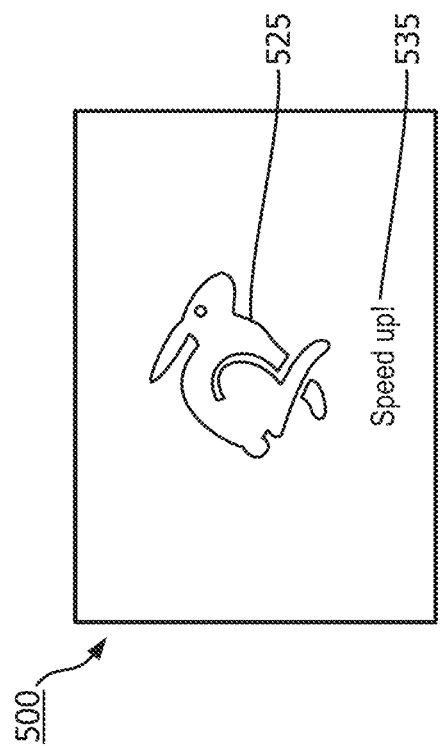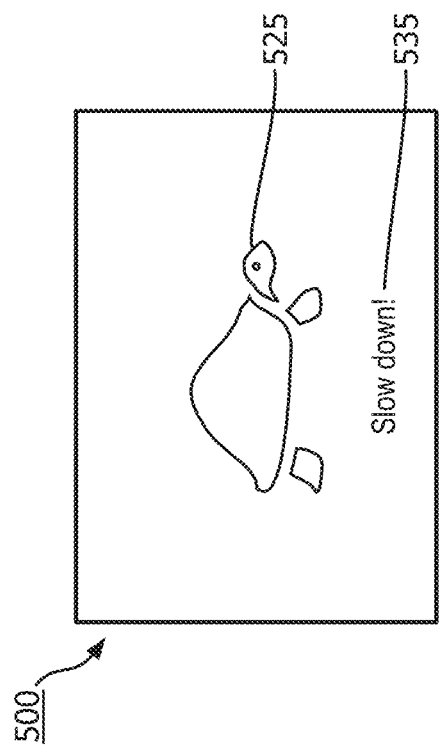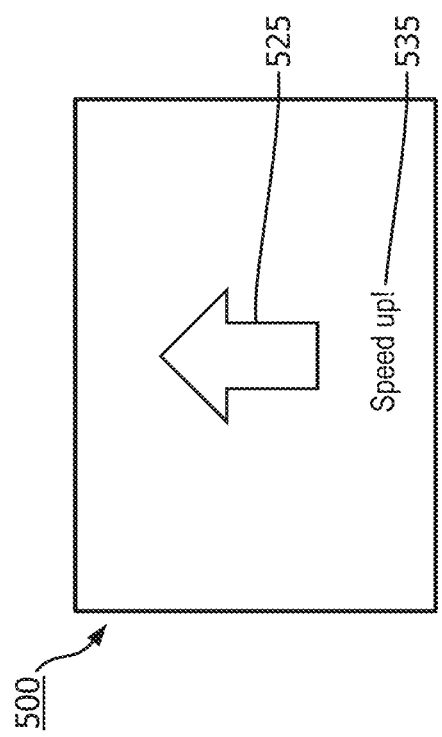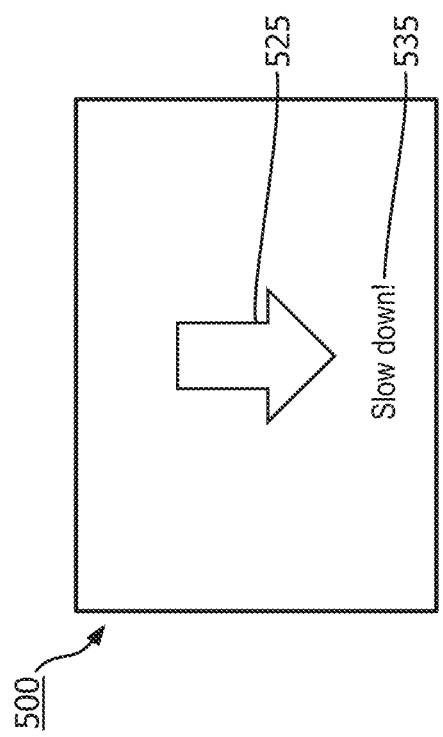

INTRAVASCULAR DEVICE MOVEMENT SPEED GUIDANCE AND ASSOCIATED DEVICES, SYSTEMS, AND METHODS

TECHNICAL FIELD

The present disclosure relates generally to the field of intravascular medical instruments used to assess the severity of a blockage or other restriction to the flow of fluid, such as blood, through a vessel. Aspects of the present disclosure include continuously calculating a movement speed of an intravascular instrument during an intravascular procedure and providing a user with real-time feedback and guidance for achieving a target movement speed.

BACKGROUND

Cardiovascular diseases (CVD) have been on a steep rise since the last decade. The death toll recorded in 2008 was 17.3 million (about 30% of global deaths) and is estimated to reach 23.3 million by 2030. Heart disease and stroke form the major contributors to total loss due to CVD with 7.3 million and 6.2 million deaths respectively. Developing and under-developed nations of the world bear a greater part (almost 80%) of the total CVD burden. The national census of India 2010-11, recorded a staggering 0.3 million deaths due to diseases of circulatory system which comprised 29.8% of the total deaths. One major cause of CVD is the presence of flow reducing blockages or lesions within blood vessels. For example, accumulation of plaque inside blood vessels can eventually cause occlusion of the blood vessels through the formation of a partial or even a complete blockage. The formation of such blockages can be life-threatening, and surgical intervention is often required to save the lives of afflicted individuals.

Currently accepted techniques for assessing the severity of a stenosis in a blood vessel, including ischemia causing lesions, include fractional flow reserve (FFR) and iFR (instant wave-free ratio). FFR is a calculation of the ratio of a distal pressure measurement (taken on the distal side of the stenosis) relative to a proximal pressure measurement (taken on the proximal side of the stenosis). iFR is a calculation of the ratio of a distal pressure measurement relative to a proximal pressure measurement using pressure measurements obtained during a diagnostic window of heartbeat/cardiac cycle when resistance is naturally constant and minimized. FFR and iFR provide an index of stenosis severity that allows determination as to whether the blockage limits blood flow within the vessel to an extent that treatment is required.

Given the severity and widespread occurrence of CVD, there remains a need for improved devices, systems, and methods for assessing blockages in a vessel and, in particular, a stenosis in a blood vessel.

SUMMARY

Aspects of the present disclosure include a medical processing unit providing a user with guidance for achieving a target movement speed of an intravascular instrument during an intravascular procedure, e.g., a pullback operation. For example, embodiments of the present disclosure include the medical processing unit tracking the intravascular instrument in radiographic images and using said tracking to calculate a movement speed of the intravascular instrument as it moves through a body lumen such as a blood vessel. The medical processing unit may then provide guidance to a user to assist the user in achieving the target movement speed. In that regard, the medical processing unit may instruct the user to increase, decrease, or maintain speed in order to achieve the target movement speed. Such guidance advantageously increases the likelihood that the intravascular instrument will be moved at a suitable speed for intravascular data acquisition and co-registration of said intravascular data with the radiographic images. Accordingly, such guidance also advantageously improves efficiency by reducing the likelihood that an intravascular procedure will be repeated on account of poor data and/or inaccurate co-registration. The devices, systems, and associated methods of the present disclosure overcome one or more of the shortcomings of the prior art.

In one embodiment, a medical system is disclosed. The medical system comprises a medical processing unit in communication with an intravascular instrument configured to be moved longitudinally within a body lumen and in further communication with a radiographic imaging source configured to obtain radiographic images of the intravascular instrument while the intravascular instrument is moved longitudinally within the body lumen. The medical processing unit is configured to: receive radiographic images obtained by the radiographic imaging source, track the intravascular instrument within the radiographic images while the intravascular instrument is moved longitudinally within the body lumen, calculate a movement speed based on the tracking, compare the calculated movement speed to a predefined target movement speed, generate a speed-adjustment suggestion based on the comparison, and output the speed-adjustment suggestion to a display for review by a user.

In some embodiments, the predefined target movement speed is between 1 and 3 millimeters per second, inclusive. In some embodiments, calculating the movement speed comprises compensating for motion of a heartbeat. In some embodiments, the intravascular instrument comprises an intravascular ultrasound (IVUS) catheter. In some embodiments, the intravascular instrument comprises a pressure sensing guidewire. In some embodiments, the intravascular instrument comprises a radiopaque marker, and wherein tracking the intravascular instrument within the radiographic images comprises tracking the radiopaque marker within the radiographic images. In some embodiments, the speed-adjustment suggestion comprises a suggestion to increase the speed at which the intravascular instrument is moved within the body lumen when the calculated movement speed is below the target movement speed. In some embodiments, the speed-adjustment suggestion comprises a suggestion to decrease the speed at which the intravascular instrument is moved within the body lumen when the calculated movement speed is above the target movement speed. In some embodiments, the speed-adjustment suggestion comprises a suggestion to maintain the speed at which the intravascular instrument is moved within the body lumen when the calculated movement speed matches the target movement speed. In some embodiments, calculating the movement speed comprises accounting for movement of the intravascular instrument through the body lumen in a Z-plane. In some embodiments, accounting for movement of the intravascular instrument through the body lumen in a Z-plane is based on an analysis of radiographic images obtained during biplane angiography. In some embodiments, accounting for movement of the intravascular instrument through the body lumen in a Z-plane is based on an analysis of anatomical data relating to the structure of the body lumen.

In one embodiment, a method is disclosed. The method comprises receiving, by a medical processing unit in communication with a radiographic imaging source, radiographic images of an intravascular instrument within a body lumen, the radiographic images obtained by the radiographic imaging source, tracking, by the medical processing unit, the intravascular instrument within the radiographic images while the intravascular instrument is moved longitudinally within the body lumen, calculating, by the medical processing unit, a movement speed based on the tracking, comparing, by the medical processing unit, the calculated movement speed to a predefined target movement speed, generating, by the medical processing unit, a speed-adjustment suggestion based on the comparison, and outputting, by the medical processing unit, the speed-adjustment suggestion to a display for review by a user.

In some embodiments, the predefined target movement speed comprises a target range between 1 and 3 millimeters per second, inclusive. In some embodiments, the speed-adjustment suggestion comprises a graphic image configured to instruct the user to increase, decrease, or maintain the speed at which the intravascular instrument is moved within the body lumen. In some embodiments, the speed-adjustment suggestion comprises textual instructions to increase, decrease, or maintain the speed at which the intravascular instrument is moved within the body lumen. In some embodiments, the speed-adjustment suggestion comprises a suggestion to repeat a pullback operation. In some embodiments, the intravascular instrument comprises an intravascular ultrasound (IVUS) catheter. In some embodiments, the intravascular instrument comprises a pressure sensing guidewire. In some embodiments, calculating the movement speed comprises compensating for motion of a heartbeat.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

Illustrative embodiments of the present disclosure will be described with reference to the accompanying drawings, of which:

FIG. 5A is a diagrammatic, schematic side view of an intravascular instrument according to an embodiment of the present disclosure.

FIG. 5B is a diagrammatic, schematic side view of an intravascular instrument according to an embodiment of the present disclosure.

FIG. 8A is a diagrammatic, schematic view of a display showing a speed-adjustment suggestion according to an embodiment of the present disclosure.

FIG. 8B is a diagrammatic, schematic view of a display showing a speed-adjustment suggestion according to an embodiment of the present disclosure.

FIG. 8C is a diagrammatic, schematic view of a display showing a speed-adjustment suggestion according to an embodiment of the present disclosure.

FIG. 8D is a diagrammatic, schematic view of a display showing a speed-adjustment suggestion according to an embodiment of the present disclosure.

DETAILED DESCRIPTION

Figure 1:
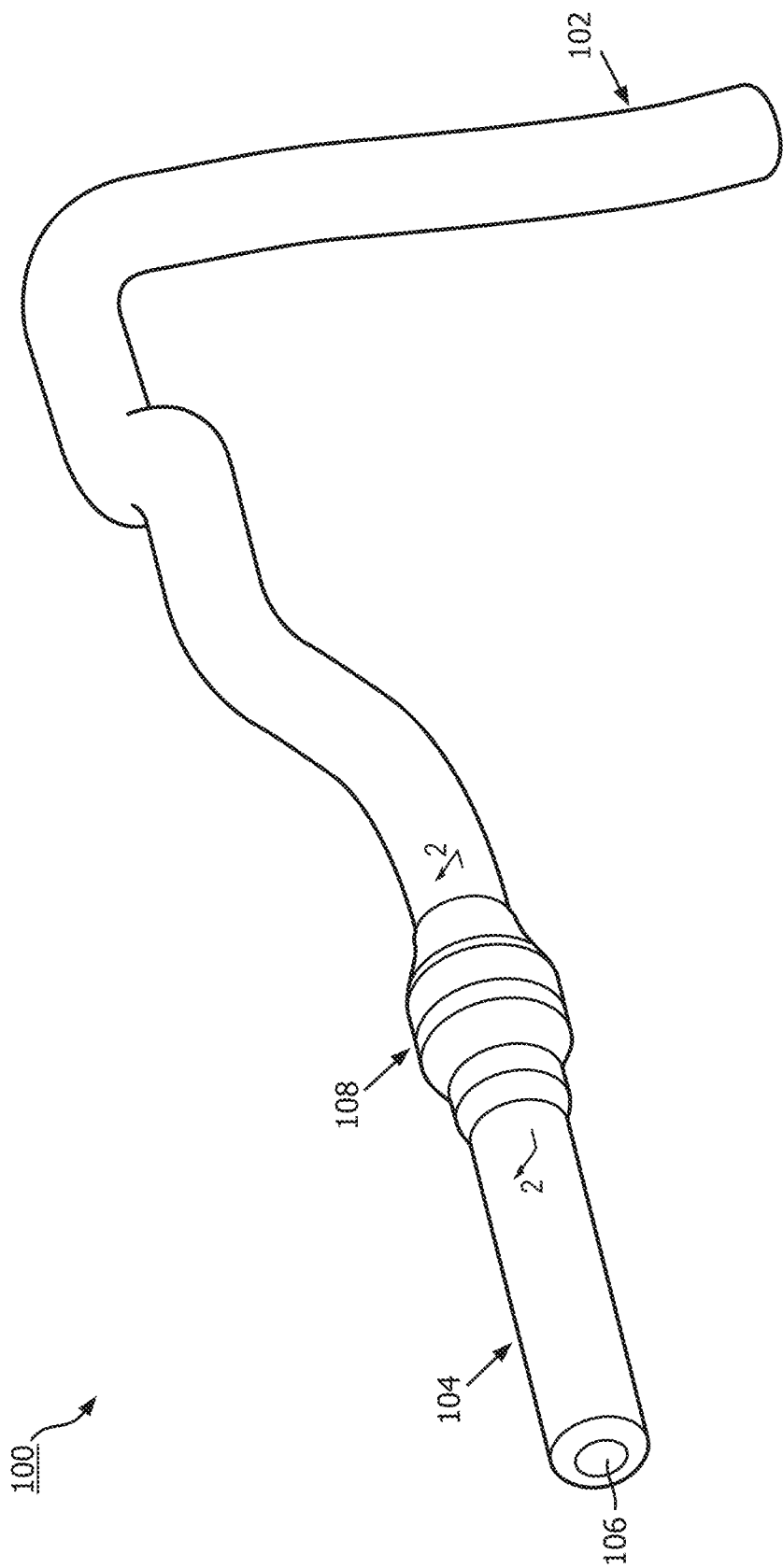
FIG. 1 is a diagrammatic perspective view of a vessel having a stenosis according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. For the sake of brevity, the numerous iterations of these combinations will not be described separately.

Figure 2:
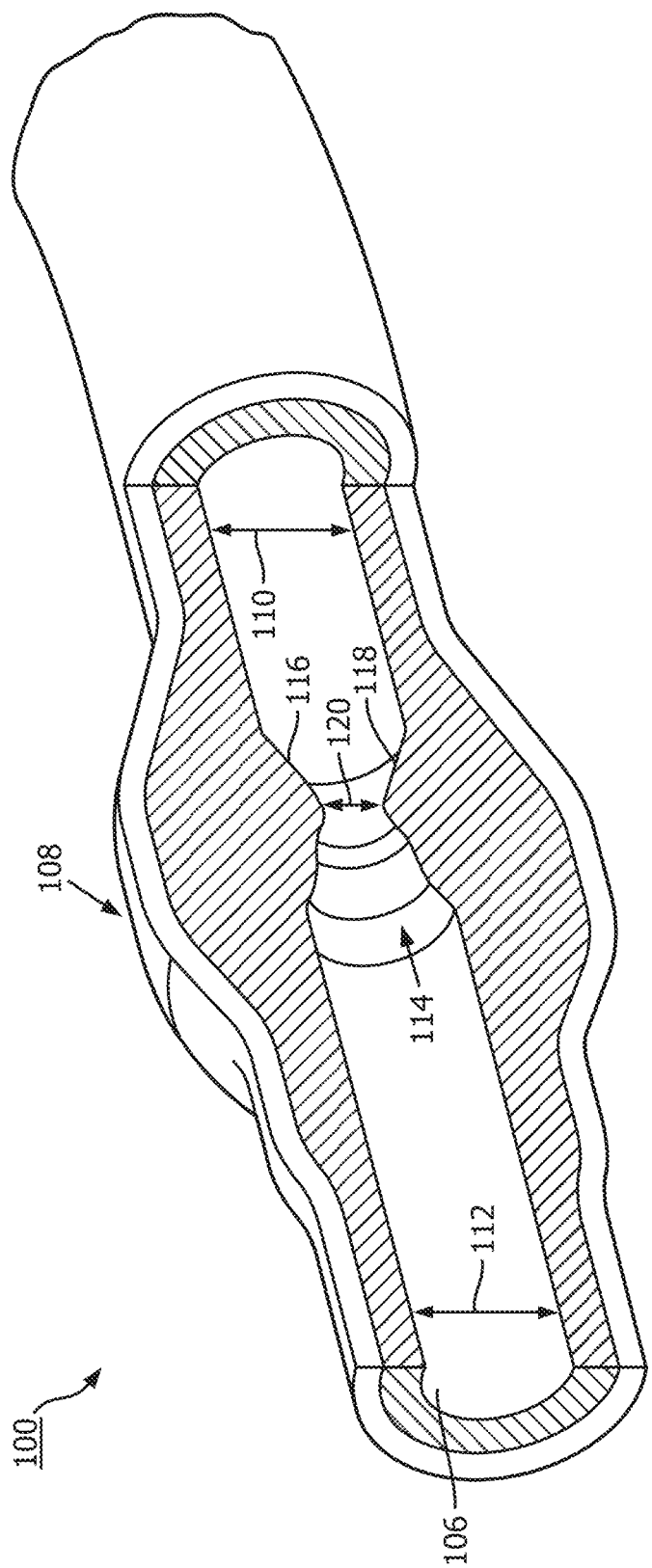
FIG. 2 is a diagrammatic, partial cross-sectional perspective view of a portion of the vessel of FIG. 1 taken along section line 2-2 of FIG. 1.

Referring to FIG. 1 and FIG. 2, shown therein is a vessel 100 having a stenosis according to an embodiment of the present disclosure. In that regard, FIG. 1 is a diagrammatic perspective view of the vessel 100, and FIG. 2 is a partial cross-sectional perspective view of a portion of the vessel 100 taken along section line 2-2 of FIG. 1. Referring more specifically to FIG. 1, the vessel 100 includes a proximal portion 102 and a distal portion 104. A lumen 106 extends along the length of the vessel 100 between the proximal portion 102 and the distal portion 104. The lumen 106 is configured to allow the flow of fluid through the vessel. In some instances, the vessel 100 is a systemic blood vessel. In some particular instances, the vessel 100 is a coronary artery. In such instances, the lumen 106 is configured to facilitate the flow of blood through the vessel 100.

As shown, the vessel 100 includes a stenosis 108 between the proximal portion 102 and the distal portion 104. Stenosis 108 is generally representative of any blockage or other structural arrangement that results in a restriction to the flow of fluid through the lumen 106 of the vessel 100. Embodiments of the present disclosure are suitable for use in a wide variety of vascular applications, including without limitation coronary, peripheral (including but not limited to lower limb, carotid, and neurovascular), renal, and/or venous. Where the vessel 100 is a blood vessel, the stenosis 108 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. It is understood that the concepts of the present disclosure are applicable to virtually any type of blockage or other narrowing of a vessel that results in decreased fluid flow.

Referring more particularly to FIG. 2, the lumen 106 of the vessel 100 has a diameter 110 proximal of the stenosis 108 and a diameter 112 distal of the stenosis 108. In some instances, the diameters 110 and 112 may be substantially equal to one another. In that regard, the diameters 110 and 112 are intended to represent healthy portions, or at least healthier portions, of the lumen 106 in comparison to stenosis 108. Accordingly, these healthier portions of the lumen 106 are illustrated as having a substantially constant cylindrical profile and, as a result, the height or width of the lumen has been referred to as a diameter. However, it is understood that in many instances these portions of the lumen 106 will also have plaque buildup, a non-symmetric profile, and/or other irregularities, but to a lesser extent than stenosis 108 and, therefore, will not have a cylindrical profile. In such instances, the diameters 110 and 112 are understood to be representative of a relative size or cross-sectional area of the lumen and do not imply a circular cross-sectional profile.

As shown in FIG. 2, stenosis 108 includes plaque buildup 114 that narrows the lumen 106 of the vessel 100. In some instances, the plaque buildup 114 may not have a uniform or symmetrical profile, making angiographic evaluation of such a stenosis potentially unreliable. In the illustrated embodiment, the plaque buildup 114 includes an upper portion 116 and an opposing lower portion 118. The lower portion 118 has an increased thickness relative to the upper portion 116 that results in a non-symmetrical and non-uniform profile relative to the portions of the lumen proximal and distal of the stenosis 108. As shown, the plaque buildup 114 decreases the available space for fluid to flow through the lumen 106. In particular, the cross-sectional area of the lumen 106 is decreased by the plaque buildup 114. At the narrowest point between the upper and lower portions 116, 118 the lumen 106 has a height 120, which is representative of a reduced size or cross-sectional area relative to the diameters 110 and 112 proximal and distal of the stenosis 108. Note that the stenosis 108, including plaque buildup 114, is exemplary in nature and should not be considered limiting in any way. In that regard, it is understood that the stenosis 108 has other shapes and/or compositions that limit the flow of fluid through the lumen 106 in other instances. While the vessel 100 is illustrated in FIG. 1 and FIG. 2 as having a single stenosis 108 and the description of the embodiments below is primarily made in the context of a single stenosis, it is nevertheless understood that the devices, systems, and methods described herein have similar application for a vessel having multiple stenosis regions.

Figure 3:
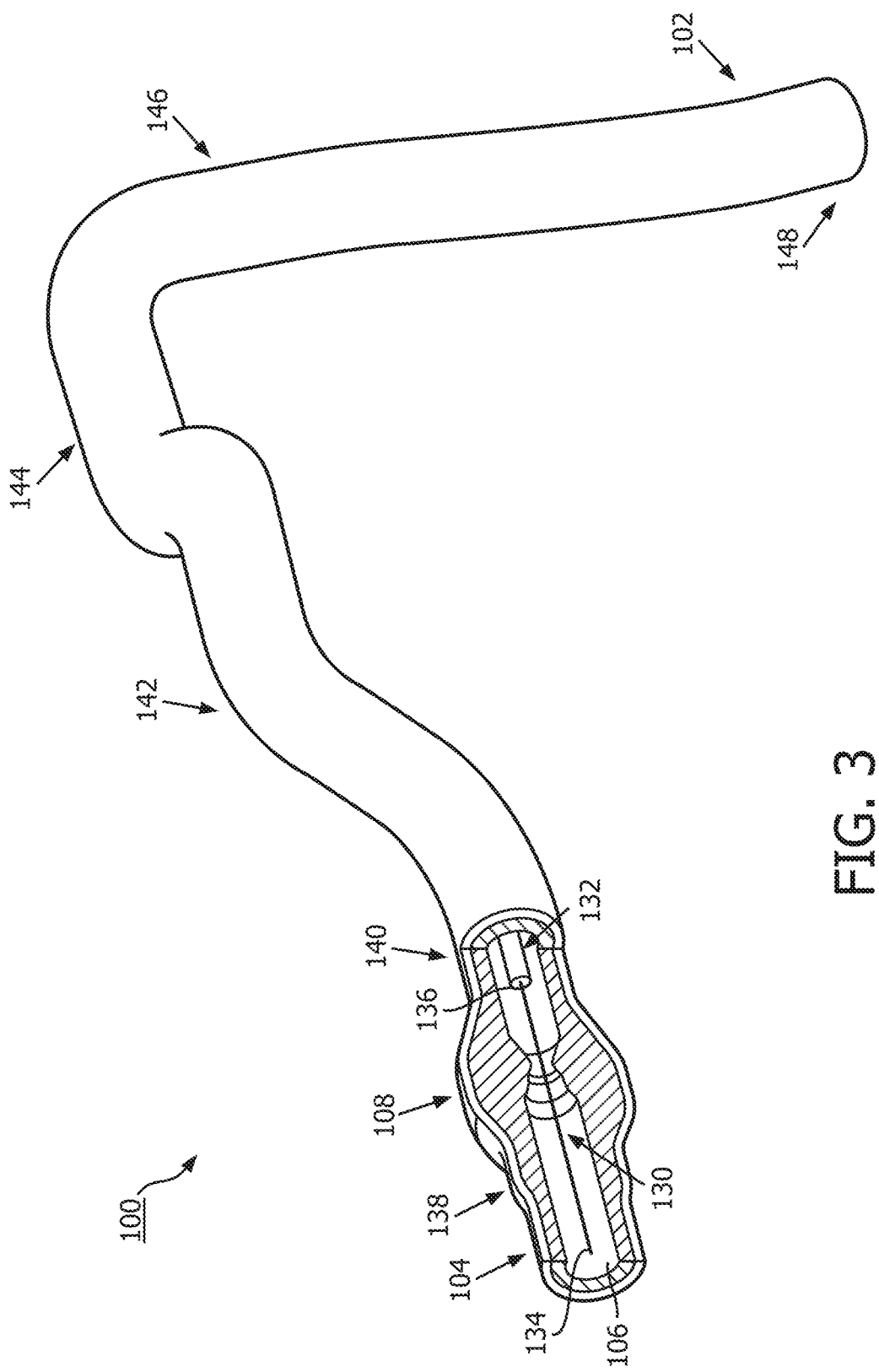
FIG. 3 is a diagrammatic, partial cross-sectional perspective view of the vessel of FIG. 1 and FIG. 2 with instruments positioned therein according to an embodiment of the present disclosure.

Referring now to FIG. 3, the vessel 100 is shown with instruments 130 and 132 positioned therein according to an embodiment of the present disclosure. In general, instruments 130 and 132 may comprise any form of device, instrument, or probe sized and shaped to be positioned within a vessel. In the illustrated embodiment, instrument 130 is generally representative of a guide wire, and instrument 132 is generally representative of a catheter or guide catheter. Generally, the instruments 130, 132 can include a flexible elongate member including a proximal portion and a distal portion. In that regard, instrument 130 may extend through a central lumen of instrument 132. However, in other embodiments, the instruments 130 and 132 may take other forms. The instruments 130 and 132 may take similar form in some embodiments. For example, in some instances, both instruments 130 and 132 may comprise guide wires. In other instances, both instruments 130 and 132 may comprise catheters. On the other hand, the instruments 130 and 132 may take different forms in some embodiments, such as the illustrated embodiment, where one of the instruments comprises a catheter and the other a guide wire. Further, in some instances, the instruments 130 and 132 may be disposed coaxial with one another, as shown in the illustrated embodiment of FIG. 3. In other instances, one of the instruments may extend through an off-center lumen of the other instrument. In yet other instances, the instruments 130 and 132 may extend side-by-side. In some particular embodiments, at least one of the instruments may comprise a rapid-exchange device, such as a rapid-exchange catheter. In such embodiments, the other instrument may comprise a buddy wire or other device configured to facilitate the introduction and removal of the rapid-exchange device. Further still, in other instances, a single instrument may be utilized instead of two separate instruments 130 and 132. In that regard, the single instrument may incorporate aspects of the functionalities (e.g., data acquisition) of both instruments 130 and 132 in some embodiments.

Instrument 130 may be configured to obtain diagnostic information about the vessel 100. While, in some contexts, diagnostic information may comprise diagnostic data, biological information, biological data, cardiovascular information, cardiovascular data, and/or other information or data, for the purposes of the present disclosure, the term "diagnostic information" will be used. Diagnostic information may be gathered continuously, approximately every 0.01 seconds, approximately every 0.1 seconds, approximately every 0.25 seconds, approximately every 0.5 seconds, approximately once per second, approximately once every two seconds, approximately once every 5 seconds, approximately once every 10 seconds, approximately once per heartbeat, and/or over some other timeframe. It is also contemplated that diagnostic information may be gathered in response to a trigger, in response to a command, or in response to a request. The diagnostic information may include one or more of pressure, flow (velocity), images (including images obtained using ultrasound (e.g., IVUS), OCT, thermal, and/or other imaging techniques), temperature, heart rate, electrical activity, and/or combinations thereof.

Accordingly, the instrument 130 may include one or more sensors, transducers, and/or other monitoring elements configured to obtain the diagnostic information about the vessel. The one or more sensors, transducers, and/or other monitoring elements may be positioned adjacent a distal portion of the instrument 130. The sensors, transducers, and/or other monitoring elements may be described with reference to an aspect of their implementation. For example, a pressure sensor may comprise a sensor configured to measure a pressure. In another example, an aortic transducer may comprise a transducer located in the aorta and/or interacting with diagnostic information pertaining to the aorta. In some instances, the transducer, such as an aortic transducer, can be positioned outside of the patient body and/or at a proximal portion of the instrument 130. For example, the transducer can be in fluid communication with a pressure sensing location at a distal portion of instrument 130 that is positioned within the patient body. The pressure at the pressure sensing location within patient body can be measured by the aortic transducer based on the fluid communication. In some instances, the one or more sensors, transducers, and/or other monitoring elements may be positioned less than 30 cm, less than 10 cm, less than 5 cm, less than 3 cm, less than 2 cm, and/or less than 1 cm from a distal tip 134 of the instrument 130. In an embodiment, at least one of the one or more sensors, transducers, and/or other monitoring elements may be positioned at the distal tip of the instrument 130.

The instrument 130 may include at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element may be implemented as a solid-state component manufactured using semiconductor and/or other suitable manufacturing techniques. Examples of commercially available guide wire products that include suitable pressure monitoring elements include, without limitation, the PrimeWire PRESTIGE® pressure guide wire, the PrimeWire® pressure guide wire, and the ComboWire® XT pressure and flow guide wire, each available from Volcano Corporation, as well as the PressureWire™ Certus guide wire and the PressureWire™ Aeris guide wire, each available from St. Jude Medical, Inc. The instrument 130 may be sized such that it can be positioned through the stenosis 108 without significantly impacting fluid flow across the stenosis, which would impact the distal pressure reading. Accordingly, in some instances the instrument 130 may have an outer diameter of 0.018" or less. In some embodiments, the instrument 130 may have an outer diameter of 0.014" or less.

Instrument 132 may also be configured to obtain diagnostic information about the vessel 100. In some instances, instrument 132 may be configured to obtain the same diagnostic information as instrument 130. In other instances, instrument 132 may be configured to obtain different diagnostic information than instrument 130, which may include additional diagnostic information, less diagnostic information, and/or alternative diagnostic information. Diagnostic information may be gathered continuously, approximately every 0.01 seconds, approximately every 0.1 seconds, approximately every 0.25 seconds, approximately every 0.5 seconds, approximately once per second, approximately once every two seconds, approximately once every 5 seconds, approximately once every 10 seconds, approximately once per heartbeat, and/or over some other timeframe. It is also contemplated that diagnostic information may be gathered in response to a trigger, in response to a command, and/or in response to a request. The diagnostic information obtained by instrument 132 may include one or more of pressure, flow (velocity), images (including images obtained using ultrasound (e.g., IVUS), OCT, thermal, and/or other imaging techniques), temperature, or combinations thereof.

Instrument 132 may include one or more sensors, transducers, and/or other monitoring elements configured to obtain this diagnostic information. In an embodiment, the one or more sensors, transducers, and/or other monitoring elements may be positioned adjacent a distal portion of the instrument 132. The sensors, transducers, and/or other monitoring elements may be described with reference to an aspect of their implementation. For example, a pressure sensor may comprise a sensor configured to measure a pressure. In another example, an aortic transducer may comprise a transducer located in the aorta and/or interacting with diagnostic information pertaining to the aorta. In some instances, the transducer, such as an aortic transducer, can be positioned outside of the patient body and/or at a proximal portion of the instrument 130. For example, the transducer can be in fluid communication with a pressure sensing location at a distal portion of instrument 132 that is positioned within the patient body. The pressure at the pressure sensing location within patient body can be measured by the aortic transducer based on the fluid communication. The one or more sensors, transducers, and/or other monitoring elements may be positioned less than 30 cm, less than 10 cm, less than 5 cm, less than 3 cm, less than 2 cm, and/or less than 1 cm from a distal tip 136 of the instrument 132. In some instances, at least one of the one or more sensors, transducers, and/or other monitoring elements may be positioned at the distal tip of the instrument 132.

Similar to instrument 130, instrument 132 may also include at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element may be implemented as a solid-state component manufactured using semiconductor and/or other suitable manufacturing techniques. Millar catheters may be utilized in some embodiments. Currently available catheter products suitable for use with one or more of Philips's Xper Flex Cardio Physiomonitoring System, GE's Mac-Lab XT and XTi hemodynamic recording systems, Siemens's AXIOM Sensis XP VC11, McKesson's Horizon Cardiology Hemo, and Mennen's Horizon XVu Hemodynamic Monitoring System and include pressure monitoring elements can be utilized for instrument 132 in some instances.

In accordance with aspects of the present disclosure, at least one of the instruments 130 and 132 may be configured to monitor a pressure, e.g., a blood pressure, within the vessel 100 distal of the stenosis 108 and at least one of the instruments 130 and 132 may be configured to monitor a pressure within the vessel proximal of the stenosis. In that regard, the instruments 130, 132 may be sized and shaped to allow positioning of the at least one element configured to monitor pressure within the vessel 100 to be positioned proximal and/or distal of the stenosis 108 as appropriate based on the configuration of the devices. FIG. 3 illustrates a position 138 suitable for measuring pressure distal of the stenosis 108. The position 138 may be less than 5 cm, less than 3 cm, less than 2 cm, less than 1 cm, less than 5 mm, and/or less than 2.5 mm from the distal end of the stenosis 108 (as shown in FIG. 2) in some instances.

FIG. 3 also illustrates a plurality of suitable positions for measuring pressure proximal of the stenosis 108. Positions 140, 142, 144, 146, and 148 each represent a position that may be suitable for monitoring the pressure proximal of the stenosis in some instances. The positions 140, 142, 144, 146, and 148 are positioned at varying distances from the proximal end of the stenosis 108 ranging from more than 20 cm down to about 5 mm or less. The proximal pressure measurement can be spaced from the proximal end of the stenosis. Accordingly, in some instances, the proximal pressure measurement may be taken at a distance equal to or greater than an inner diameter of the lumen of the vessel from the proximal end of the stenosis. In the context of coronary artery pressure measurements, the proximal pressure measurement may be taken at a position proximal of the stenosis and distal of the aorta, within a proximal portion of the vessel. However, in some particular instances of coronary artery pressure measurements, the proximal pressure measurement may be taken from a location inside the aorta. In such instances, the pressure data obtained may be referred to as aortic pressure data. In other instances, the proximal pressure measurement may be taken at the root or ostium of the coronary artery.

Figure 4:
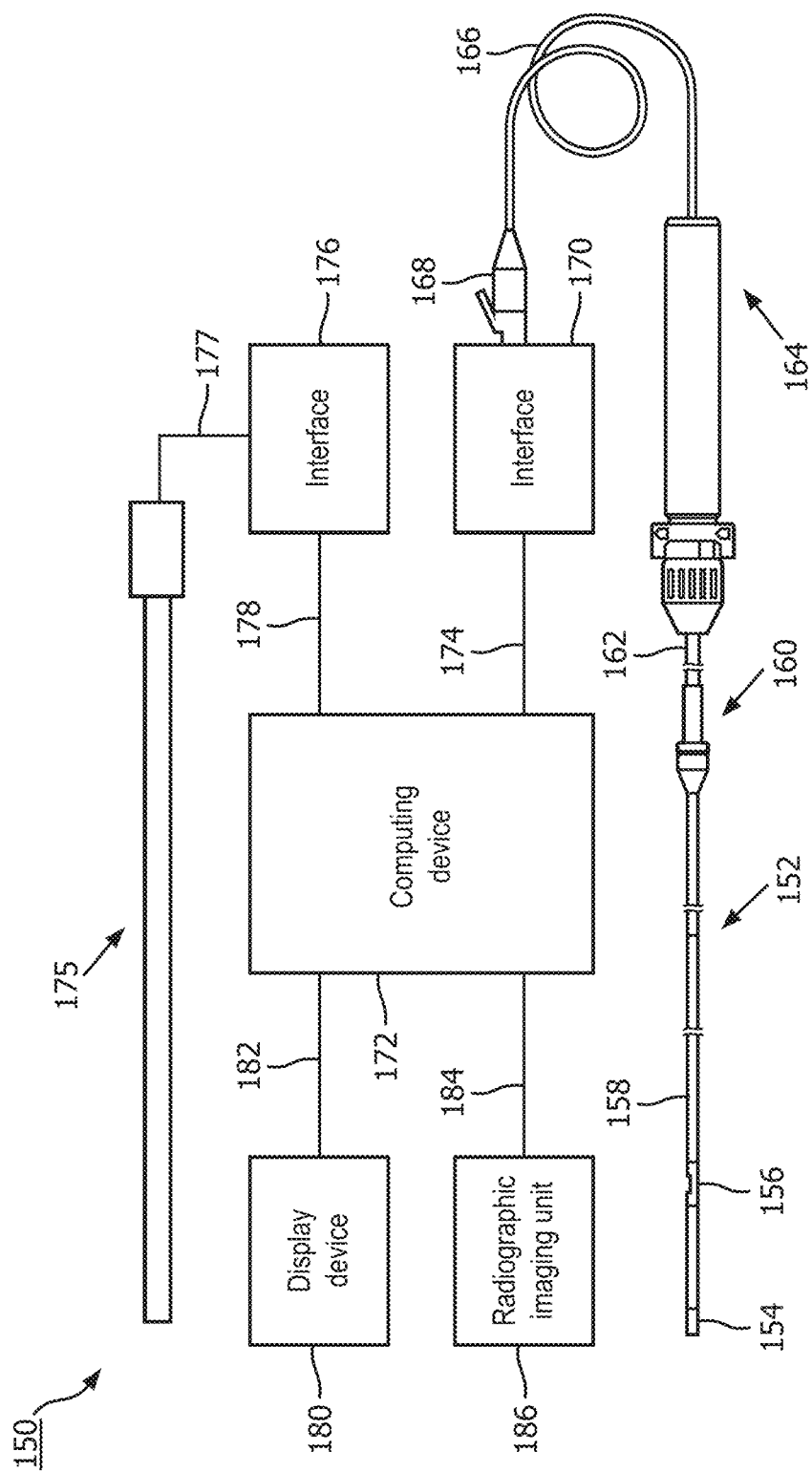
FIG. 4 is a diagrammatic, schematic view of a system according to an embodiment of the present disclosure.

Referring now to FIG. 4, shown therein is a system 150 according to an embodiment of the present disclosure. In that regard, FIG. 4 is a diagrammatic, schematic view of the system 150. As shown, the system 150 includes an instrument 152. In that regard, in some instances instrument 152 is suitable for use as at least one of instruments 130 and 132 discussed above. Accordingly, in some instances the instrument 152 includes features similar to those discussed above with respect to one or both of instruments 130 and 132. In the illustrated embodiment, the instrument 152 is a guide wire having a distal portion 154 and a housing 156 positioned adjacent the distal portion. In that regard, the housing 156 is spaced approximately 3 cm from a distal tip of the instrument 152. The housing 156 is configured to house one or more sensors, transducers, and/or other monitoring elements configured to obtain the diagnostic information about the vessel. In the illustrated embodiment, the housing 156 contains at least a pressure sensor configured to monitor a pressure within a lumen in which the instrument 152 is positioned. A shaft 158 extends proximally from the housing 156. A torque device 160 is positioned over and coupled to a proximal portion of the shaft 158. A proximal end portion 162 of the instrument 152 is coupled to a connector 164. A cable 166 extends from connector 164 to a connector 168. In some instances, connector 168 is configured to be plugged into an interface 170. In that regard, interface 170 is a patient interface module (PIM) in some instances. The cable 166 may be replaced with a wireless connection in some instances. In that regard, it is understood that various communication pathways between the instrument 152 and the interface 170 may be utilized, including physical connections (including electrical, optical, and/or fluid connections), wireless connections, and/or combinations thereof.

The interface 170 is communicatively coupled to a computing device 172 via a connection 174. Computing device 172 is generally representative of any device suitable for performing the processing and analysis techniques discussed within the present disclosure. In some embodiments, the computing device 172 includes a processor, random access memory, and a storage medium. In that regard, in some particular instances the computing device 172 is programmed to execute steps associated with the normalization, data acquisition, and data analysis described herein. Accordingly, it is understood that any steps related to normalization, data acquisition, data processing, instrument control, and/or other processing or control aspects of the present disclosure may be implemented by the computing device 172 using corresponding instructions stored on or in a non-transitory computer readable medium accessible by the computing device 172. In some instances, the computing device 172 is a console device. In some particular instances, the computing device 172 is similar to the s5 Imaging System or the s5i Imaging System, each available from Volcano Corporation. In some instances, the computing device 172 is portable (e.g., handheld, on a rolling cart, etc.). In some instances, all or a portion of the computing device 172 can be implemented as a bedside controller such that one or more processing steps described herein can be performed by processing component(s) of the bedside controller. An exemplary bedside controller is described in U.S. Provisional Application No. 62/049,265, titled "Bedside Controller for Assessment of Vessels and Associated Devices, Systems, and Methods," and filed Sep. 11, 2014, the entirety of which is hereby incorporated by reference. Further, it is understood that in some instances the computing device 172 comprises a plurality of computing devices and/or virtual computing devices. In that regard, it is particularly understood that the different processing and/or control aspects of the present disclosure may be implemented separately or within predefined groupings using a plurality of computing devices and/or virtual computing devices. Any divisions and/or combinations of the processing and/or control aspects described below across multiple computing devices and/or virtual computing devices are within the scope of the present disclosure.

Together, connector 164, cable 166, connector 168, interface 170, and connection 174 facilitate communication between the one or more sensors, transducers, and/or other monitoring elements of the instrument 152 and the computing device 172. However, this communication pathway is exemplary in nature and should not be considered limiting in any way. In that regard, it is understood that any communication pathway between the instrument 152 and the computing device 172 may be utilized, including physical connections (including electrical, optical, and/or fluid connections), wireless connections, and/or combinations thereof. In that regard, it is understood that the connection 174 is wireless in some instances. In some instances, the connection 174 includes a communication link over a network (e.g., intranet, internet, telecommunications network, and/or other network). In that regard, it is understood that the computing device 172 is positioned remote from an operating area where the instrument 152 is being used in some instances. Having the connection 174 include a connection over a network can facilitate communication between the instrument 152 and the remote computing device 172 regardless of whether the computing device is in an adjacent room, an adjacent building, or in a different state/country. Further, it is understood that the communication pathway between the instrument 152 and the computing device 172 is a secure connection in some instances. Further still, it is understood that, in some instances, the data communicated over one or more portions of the communication pathway between the instrument 152 and the computing device 172 is encrypted.

The system 150 also includes an instrument 175. In that regard, in some instances instrument 175 is suitable for use as at least one of instruments 130 and 132 discussed above.

Accordingly, in some instances the instrument 175 includes features similar to those discussed above with respect to one or both of instruments 130 and 132. In the illustrated embodiment, the instrument 175 is a catheter-type device. In that regard, the instrument 175 includes one or more sensors, transducers, and/or other monitoring elements adjacent a distal portion of the instrument 175 configured to obtain the diagnostic information about the vessel. In the illustrated embodiment, the instrument 175 includes a pressure sensor configured to monitor a pressure within a lumen in which the instrument 175 is positioned. The instrument 175 is in communication with an interface 176 via connection 177. In some instances, interface 176 is a hemodynamic monitoring system or other control device, such as Siemens AXIOM Sensis, Mennen Horizon XVu, and Philips Xper IM Physiomonitoring 5. In one particular embodiment, instrument 175 is a pressure-sensing catheter that includes fluid column extending along its length. In such an embodiment, interface 176 includes a hemostasis valve fluidly coupled to the fluid column of the catheter, a manifold fluidly coupled to the hemostasis valve, and tubing extending between the components as appropriate to fluidly couple the components. In that regard, the fluid column of the catheter is in fluid communication with a pressure sensor via the valve, manifold, and tubing. In some instances, the pressure sensor is part of interface 176. In other instances, the pressure sensor is a separate component positioned between the instrument 175 and the interface 176. The interface 176 is communicatively coupled to the computing device 172 via a connection 178.

The computing device 172 is communicatively coupled to a display device 180 via a wired or wireless connection 182. In some embodiments, the display device 180 is a component of the computing device 172, while in other embodiments, the display device 180 is distinct from the computing device 172. In some embodiments, the display device 180 is implemented as a bedside controller having a touch-screen display as described, for example, in U.S. Provisional Application No. 62/049,265, titled "Bedside Controller for Assessment of Vessels and Associated Devices, Systems, and Methods," and filed Sep. 11, 2014, the entirety of which is hereby incorporated by reference herein. The computing device 172 can generate screen displays including data collected by the instruments 152 and 175 and other instruments, quantities computed based on the collected data, visualizations of the vessel in which the data is collected, and visualizations based on the collected data and computed quantities. Exemplary screen displays are illustrated in FIGS. 8A-9B. The computing device 172 can provide the display data associated with the screen displays to the display device 180.

The computing device 172 is communicatively coupled to a radiographic unit 186. For example, data obtained by the radiographic unit 186 can be directly or indirectly transmitted to and/or received by the computing device 172, e.g., via a wired or wireless connection 184. The radiographic unit 186 may obtain diagnostic information of a patient's vasculature and may communicate such diagnostic information to the computing device 172. The unit 186 can be referenced as an external imaging unit in some embodiments in that it obtains imaging data of a body lumen within the body while positioned outside of the body. In various embodiments, the diagnostic information obtained by the external imaging unit 186 may include externally-obtained angiographic images, x-ray images, CT images, PET images, MRI images, SPECT images, fluoroscopic images, radiographic images, combinations thereof and/or other two-dimensional or three-dimensional extraluminal depictions of a patient's vasculature. For example, angiographic images can be single frame, still, radiographic images of the vasculature of the patient and/or one or more intravascular devices positioned within the vasculature. For example, fluoroscopic images can be multi-frame, moving radiographic images of the vasculature and/or one or more intravascular devices positioned within the vasculature. In some cases, diagnostic information and/or data obtained by instruments 130, 132, 152, and/or 175 may be correlated or co-registered to diagnostic information such as angiographic image(s) and/or other two-dimensional or three-dimensional depictions of a patient's vasculature obtained by the radiographic unit 186. In some embodiments, the radiographic unit 186 obtains radiographic images after contrast media has been delivered into the vessel and/or other lumen. In other embodiments, the radiographic unit 186 obtains radiographic images without contrast media within the vessel and/or other lumen.

The computing device 172 can additionally be communicatively coupled to a user interface device. The user interface device permits a user to interact with the screen displays on the display device 180. For example, the user can provide a user input to modify all or a portion of the screen display using the user interface device. In some embodiments, the user interface device is a separate component from the display device 180. In other embodiments, the user interface device is part of the display device 180. For example, the user interface device can be implemented as a bedside controller having a touch-screen display as described, for example, in U.S. Provisional Application No. 62/049,265, titled "Bedside Controller for Assessment of Vessels and Associated Devices, Systems, and Methods," and filed Sep. 11, 2014, the entirety of which is hereby incorporated by reference herein. In such embodiments, a user input can be a touch input received on the touch sensitive display of the bedside controller.

Similar to the connections between instrument 152 and the computing device 172, interface 176 and connections 177 and 178 facilitate communication between the one or more sensors, transducers, and/or other monitoring elements of the instrument 175 and the computing device 172. However, this communication pathway is exemplary in nature and should not be considered limiting in any way. In that regard, it is understood that any communication pathway between the instrument 175 and the computing device 172 may be utilized, including physical connections (including electrical, optical, and/or fluid connections), wireless connections, and/or combinations thereof. In that regard, it is understood that the connection 178 is wireless in some instances. In some instances, the connection 178 includes a communication link over a network (e.g., intranet, internet, telecommunications network, and/or other network). In that regard, it is understood that the computing device 172 is positioned remote from an operating area where the instrument 175 is being used in some instances. Having the connection 178 include a connection over a network can facilitate communication between the instrument 175 and the remote computing device 172 regardless of whether the computing device is in an adjacent room, an adjacent building, or in a different state/country. Further, it is understood that the communication pathway between the instrument 175 and the computing device 172 is a secure connection in some instances. Further still, it is understood that, in some instances, the data communicated over one or more portions of the communication pathway between the instrument 175 and the computing device 172 is encrypted.

It is understood that one or more components of the system 150 are not included, are implemented in a different arrangement/order, and/or are replaced with an alternative device/mechanism in other embodiments of the present disclosure. For example, in some instances, the system 150 does not include interface 170 and/or interface 176. In such instances, the connector 168 (or other similar connector in communication with instrument 152 or instrument 175) may plug into a port associated with computing device 172. Alternatively, the instruments 152, 175 may communicate wirelessly with the computing device 172. Generally speaking, the communication pathway between either or both of the instruments 152, 175 and the computing device 172 may have no intermediate nodes (i.e., a direct connection), one intermediate node between the instrument and the computing device, or a plurality of intermediate nodes between the instrument and the computing device.

It is understood that one or more of the instruments 130, 132, 150, 152 can a guide wire, a guide catheter, a catheter, or any other suitable intraluminal device. In that regard, instruments 130, 132, 150, 152 include a flexible elongate member forming a body of the intraluminal instrument. In use, a proximal portion of the flexible elongate member is positioned outside patient's body. One, two, three, four or more sensors are coupled to the distal portion of the flexible elongate member and is configured obtain any suitable data associated with the body lumen while positioned within the body lumen. The data can include one or more of pressure, flow (velocity), images (including images obtained using ultrasound (e.g., IVUS), OCT, thermal, and/or other imaging techniques), temperature, or combinations thereof. One or more of the instruments 130, 132, 150, 152 can be an intracardiac (ICE) echocardiography catheter and/or a transesophageal echocardiography (TEE) probe. Instruments 130, 132, 150, 152 are sized and shaped, structurally arranged, and/or otherwise configured to be positioned within any suitable body lumen of a patient. The body lumen may represent fluid filled or surrounded structures, both natural and man-made. The body lumen may be a blood vessel, as an artery or a vein of a patient's vascular system, including cardiac vasculature, peripheral vasculature, neural vasculature, renal vasculature, and/or or any other suitable lumen inside the body. For example, the instruments 130, 132, 150, 152 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the instruments 130, 132, 150, 152 may be used to examine man-made structures such as, but without limitation, heart valves, stents, shunts, filters and other devices.

Referring now to FIGS. 5A and 5B, shown therein are diagrammatic, schematic side views of an intravascular instrument 202. FIGS. 5A and 5B illustrate a distal portion of the intravascular instrument 202. It is understood that, in use, the intravascular instrument 202 may be positioned within a vasculature of a patient. In an embodiment, intravascular instrument 202 may be an element of the system 150 and/or may interact with elements of the system 150. In that regard, in some instances, intravascular instrument 202 may be suitable for use as at least one of instruments 130, 132, 152, and 175 discussed above. Accordingly, in some instances the intravascular instrument 202 includes features similar to those discussed above with respect to one or more of instruments 130, 132, 152, and 175. In some cases, the intravascular instrument 202 may comprise a pressure-sensing guide wire or catheter. In some cases, the intravascular instrument 202 may comprise an IVUS guide wire or catheter.

In the illustrated embodiments, the intravascular instrument 202 comprises a sensor 210, a radiopaque region 214, and a non-radiopaque region 216. A pattern may be formed by the radiopaque region(s) 214 and non-radiopaque region(s) 216. One possible pattern is shown in FIG. 5A while a different pattern is shown in FIG. 5B. In FIG. 5A, the entire region distal to sensor 210 is radiopaque while the entire region proximal to sensor 210 is non-radiopaque. In FIG. 5B, the entire region distal to sensor 210 is radiopaque while the region proximal to sensor 210 features alternating radiopaque regions 214 and non-radiopaque regions 216.

The sensor 210 may be configured to obtain pressure data. In that regard, the sensor 210 may comprise a piezo-resistive pressure sensor, a piezo-electric pressure sensor, a capacitive pressure sensor, an electromagnetic pressure sensor, a fluid column (the fluid column being in communication with a fluid column sensor that is separate from the intravascular instrument 202 and/or positioned at a portion of intravascular instrument 202 that is proximal of the fluid column), an optical pressure sensor, and/or combinations thereof.

In some cases, sensor 210 may comprise an imaging assembly. The imaging assembly can include a transducer or a transducer array comprising a plurality of transducer elements or acoustic elements. The intravascular instrument 202 may emit ultrasonic energy from the transducer array. The ultrasonic energy is reflected by tissue structures, e.g., walls of a body lumen such as a blood vessel, surrounding the transducer array, and the ultrasound echo signals are received by the transducer array. The transducer array can include any suitable number of individual transducers between 1 acoustic element and 1000 acoustic elements, including values such as 2 acoustic elements, 4 acoustic elements, 36 acoustic elements, 64 acoustic elements, 128 acoustic elements, 500 acoustic elements, 812 acoustic elements, and/or other values both larger and smaller. The transducer array may be a phased array. In some instances, the transducer elements of the array may be arranged in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The transducer array may be divided into segments, e.g., one or more rows and/or columns, that may be independently controlled and activated. The transducer array and/or individual transducers may be arranged to emit and/or receive ultrasonic energy at an oblique angle relative to a longitudinal axis of the intravascular instrument 202. The transducers can be piezo-electric micromachined ultrasound transducers (PMUT), capacitive micromachined ultrasonic transducers (CMUT), single crystal, lead zirconate titanate (PZT), PZT composite, other suitable transducer types, and/or combinations thereof. Exemplary capacitive micromachined ultrasound transducers (cMUTs) are disclosed, for example, in U.S. application Ser. No. 14/812,792, filed Jul. 29, 2015, and titled "Intravascular Ultrasound Imaging Apparatus, Interface Architecture, and Method of Manufacturing," which is hereby incorporated by reference in its entirety. Depending on the transducer material, the manufacturing process for the transducer(s) can include dicing, kerfing, grinding, sputtering, wafer technologies (e.g., SMA, sacrificial layer deposition), other suitable processes, and/or combinations thereof.

Intravascular instrument 202 may be used to gather diagnostic information from inside a patient's vasculature, e.g., inside the aorta and/or coronary arteries. In that regard, one or more sensors of the intravascular instrument 202 may gather pressure data, flow (velocity) data, images (including images obtained using ultrasound (e.g., IVUS), OCT, thermal, and/or other imaging techniques), temperature data, or combinations thereof. In some instances, intravascular instrument 202 may be used to gather pressure data to be used in calculating a pressure ratio, an FFR value, and/or an iFR (instant wave-free ratio) value. Exemplary embodiments of determining a diagnostic window within a heartbeat cycle of a patient and calculating an iFR value based on pressure measurements obtained within the diagnostic window are described in U.S. Pat. No. 9,339,348, the entirety of which is hereby incorporated by reference. Accordingly, the intravascular instrument 202 may be arranged within a vessel having a stenosis such that the intravascular instrument 202 may measure pressure distal of the stenosis (Pd) and while another intravascular instrument may measure pressure proximal of the stenosis (Pa). In that regard, the intravascular instrument 202 may be positioned within the vessel such that the sensor 210 is distal to the stenosis.

The intravascular instrument 202 may be moved longitudinally through a patient's vasculature during acquisition of diagnostic information. In some cases, such movement may be part of a pullback operation (e.g., movement from a distal location within the vessel to a proximal location within the vessel). In other cases, such movement may comprise advancement of the intravascular instrument 202 through the vasculature (e.g., movement from a proximal location within the vessel to a distal location within the vessel). The speed of the movement may be controlled manually by a user, e.g., a physician, by acting on the proximal portion of the intravascular instrument that is disposed outside the patient body. While extant electromechanical pullback devices can control movement of the instrument 202 through the vessel, they are disfavored by users because they undesirably prolong the procedure because they must be set up and connected to the instrument 202. As a result, users may sometimes avoid obtaining valuable intraluminal info with the instrument 202 if they were required to use a pullback device. Users much prefer the simpler and faster workflow that is permitted by manual, user-controlled pullback or advancement of the instrument 202 through the body lumen.

The speed at which the intravascular instrument 202 is moved through the vasculature may affect the quality of diagnostic information obtained and may affect the efficiency of an intravascular procedure. Because a human operator is controlling the movement of the instrument 202, it can be difficult to achieve the correct speed. For example, diagnostic information may be distorted if the intravascular instrument 202 is moved too quickly. Moving the intravascular instrument 202 too quickly may also result in a lack of diagnostic information for certain portions of the vasculature, e.g., those bypassed before diagnostic information could be acquired. When diagnostic information obtained intravascularly is to be co-registered with radiographic images obtained externally, moving the intravascular instrument 202 too quickly may reduce the accuracy of the co-registration. On the other hand, moving the intravascular instrument 202 too slowly may simply prolong the intravascular procedure without improving the quality of the diagnostic information obtained or improving the accuracy of co-registration.

Accordingly, a target movement speed may be established. The target movement speed may be established by a user or may be determined automatically by a medical processing unit in communication with the intravascular instrument 202, e.g., computing device 172. The target movement speed may be a movement speed at which accurate diagnostic information may be obtained and/or a movement speed enabling accurate co-registration of intravascular data with one or more radiographic images. The medical processing unit may determine the target movement speed based on an analysis of the movement speed of past data acquisitions and the success of such data acquisitions. For example, when the medical processing unit determines that data acquisitions performed at movement speeds of 1 centimeter per second were unsuccessful, the medical processing unit may establish a target movement speed less than 1 centimeter per second. The success of data acquisition may be determined by a user, e.g., via a user indicating approval or disapproval to the medical processing unit, and/or may be determined by the medical processing unit itself, e.g., by determining that no diagnostic information was obtained for some portion of the vasculature or by determining that an intravascular procedure was repeated on account of poor data quality. In that regard, the medical processing unit may store, either locally or remotely, information indicating the movement speed and success or failure of past intravascular procedures.

The target movement speed may be a discrete value, e.g., 2 millimeters per second, or may comprise a range of acceptable values, e.g., between 1 millimeter per second and 3 millimeters per second, inclusive. In that regard, the target movement speed may be any discrete value or range of values between 0.5 millimeters per second and 10 millimeters per second, inclusive. In some cases, the target movement speed may be any discrete value or range of values between 1 millimeter per second and 5 millimeters per second, inclusive. In some cases, the target movement speed may be any discrete value or range of values between 1 millimeter per second and 3 millimeters per second, inclusive. While several exemplary discrete values and ranges are provided above, the target movement speed may in some cases be any suitable value or range of values, including values and ranges of values outside of the exemplary values and ranges set forth above. As described in greater detail below, establishment of a target speed may enable the medical processing unit to provide guidance in the form of speed-adjustment suggestions to the user.

Figure 6:
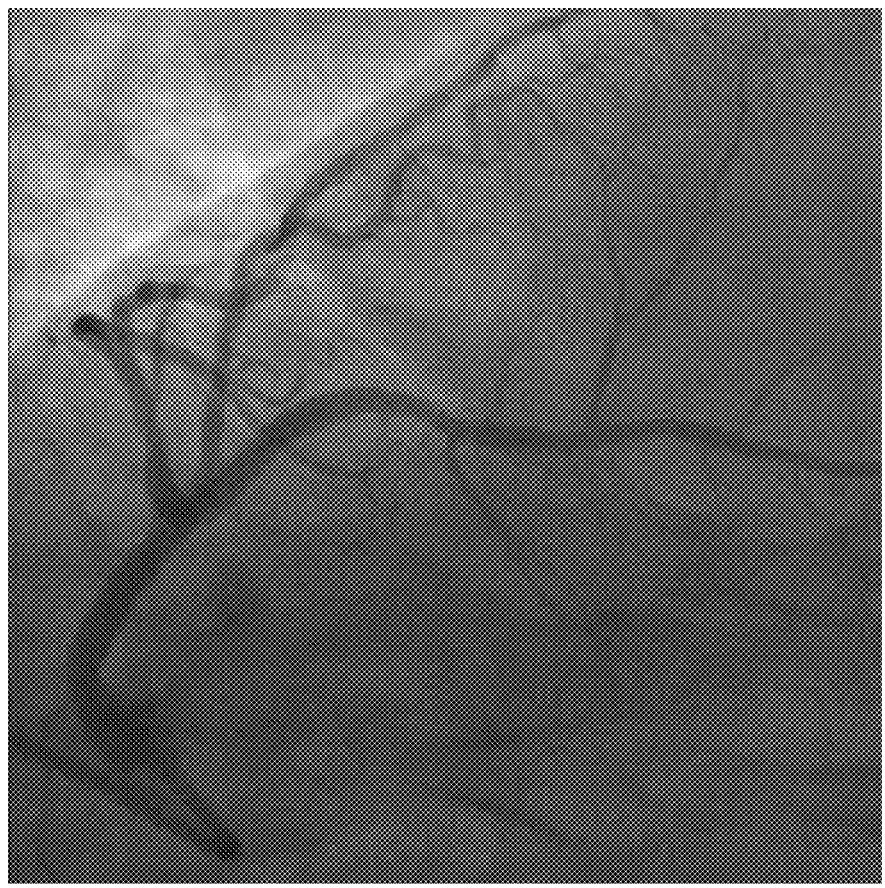
FIG. 6 is a radiographic image of a vasculature according to an embodiment of the present disclosure.

Turning now to FIG. 6, shown therein is an angiographic image 300. The angiographic image 300 may have been obtained by a radiographic imaging source, e.g., radiographic unit 186. As discussed above, the radiographic imaging source may be in communication with a medical processing unit, e.g., computing device 172. The angiographic image 300 may be obtained while a contrast agent fills the vasculature and may accordingly depict the location of various blood vessels, e.g., coronary arteries. In that regard, as described in greater detail below, the angiographic image 300 may serve as a roadmap for calculating a movement speed of an intravascular instrument and for co-registration of intravascular data with a radiographic image as shown in, for example, FIGS. 9A and 9B.

Figure 7A:
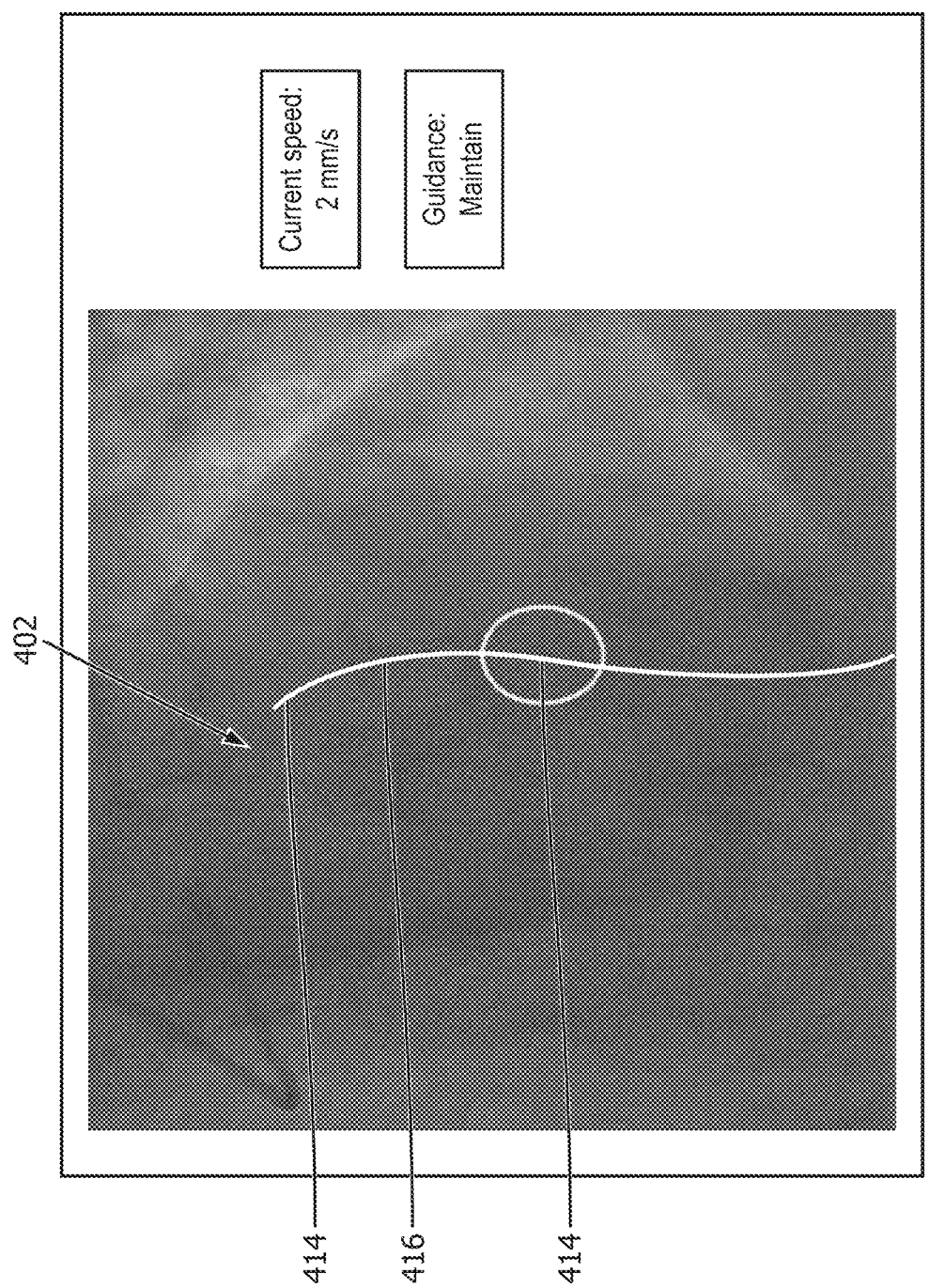
FIG. 7A is a diagrammatic, schematic view of a display showing a speed-adjustment suggestion and a radiographic image of an intravascular instrument according to an embodiment of the present disclosure.
Figure 7B:
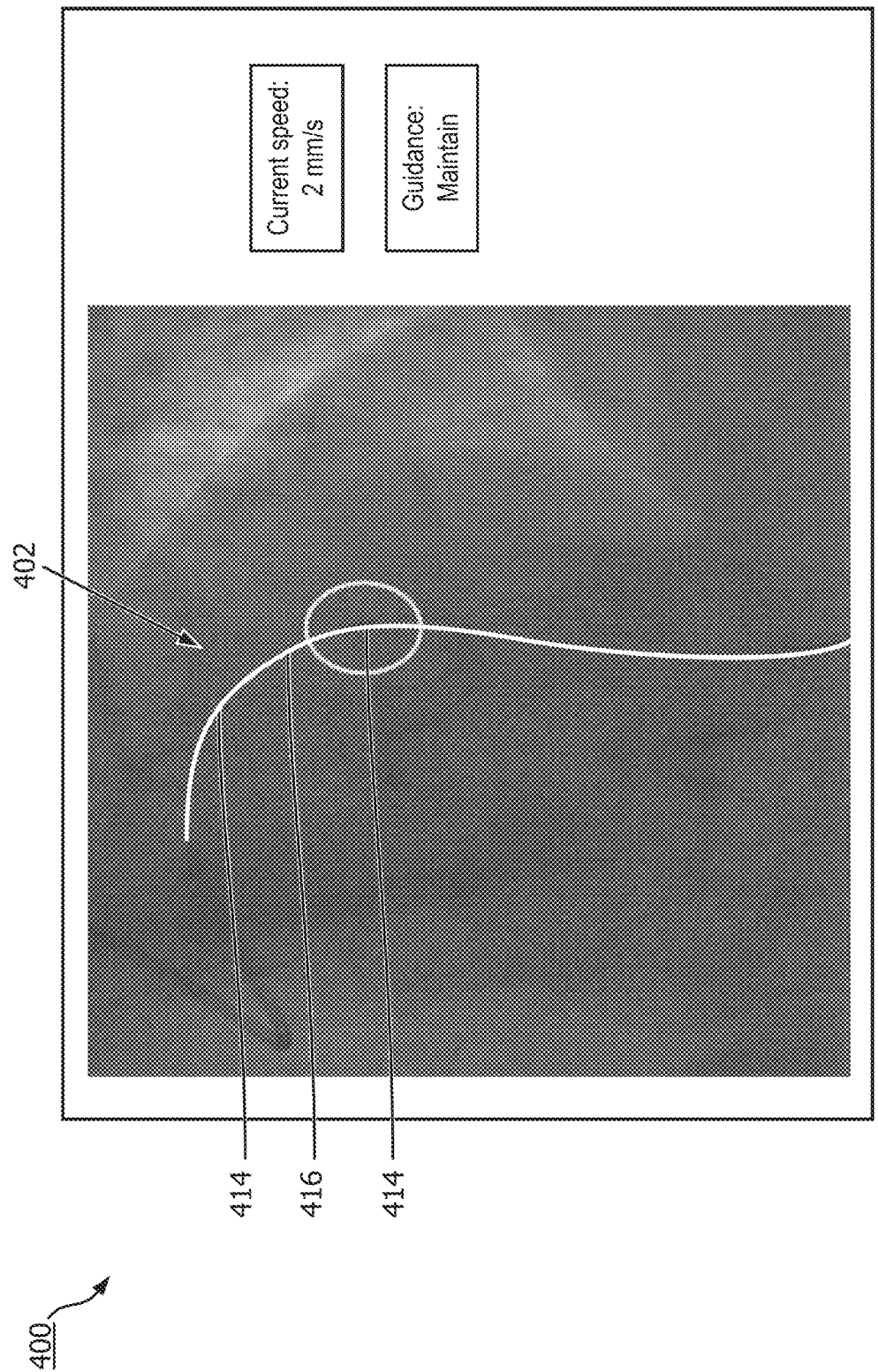
FIG. 7B is a diagrammatic, schematic view of a display showing a speed-adjustment suggestion and a radiographic image of an intravascular instrument according to an embodiment of the present disclosure.
Figure 7C:
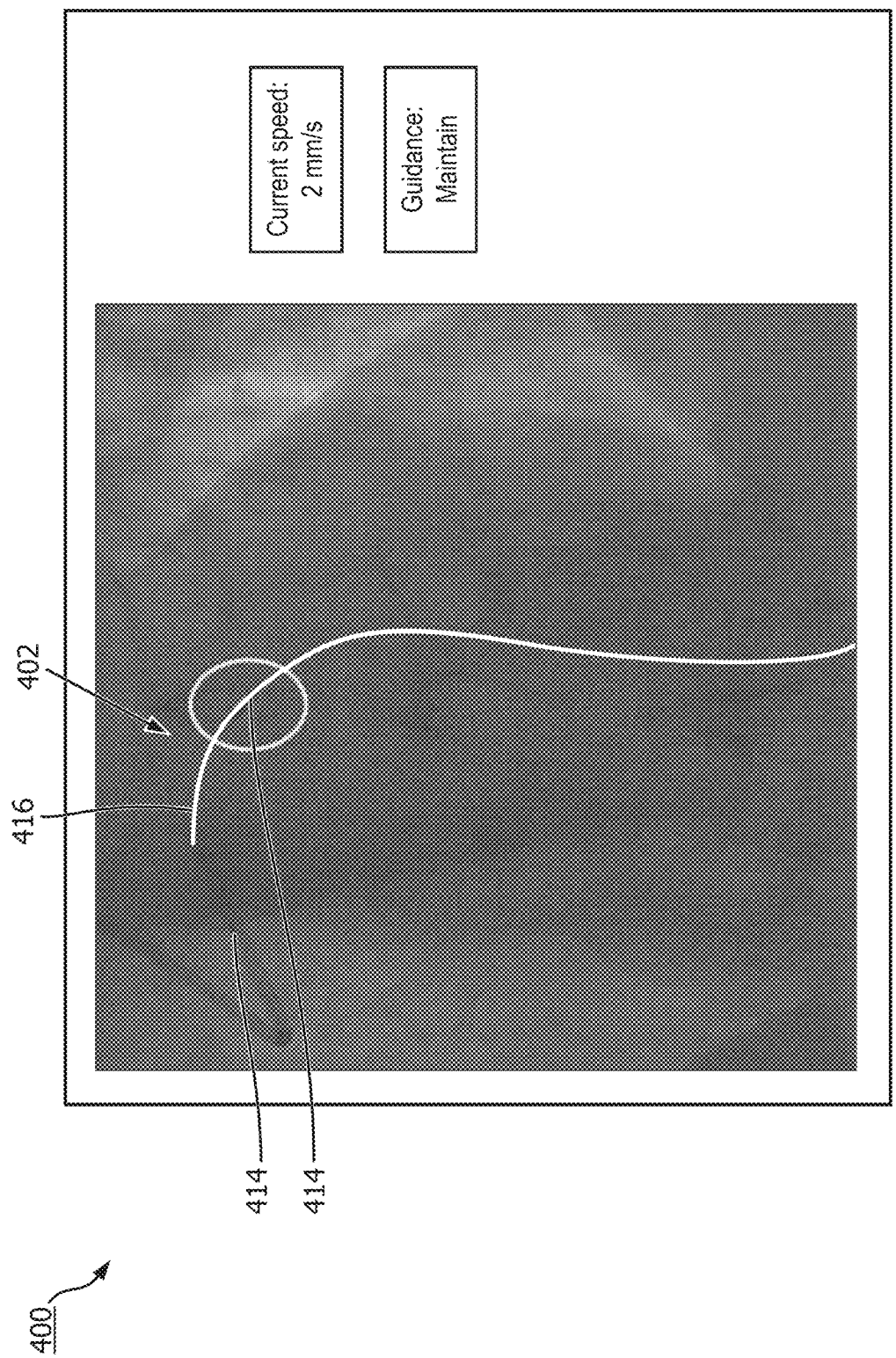
FIG. 7C is a diagrammatic, schematic view of a display showing a speed-adjustment suggestion and a radiographic image of an intravascular instrument according to an embodiment of the present disclosure.

Turning now to FIGS. 7A-7C, shown therein are a diagrammatic, schematic views of a display 400 showing a speed-adjustment suggestion and radiographic images of an intravascular instrument according to an embodiment of the present disclosure. The radiographic images illustrated in FIGS. 7A-7C are fluoroscopic images in which no contrast, or at least very little contrast, is present in the vasculature. Intravascular instrument 402 is visible in the radiographic images. FIGS. 7A-7C depict different positions of the intravascular instrument 402 as it is moved through a vessel, e.g., during an intravascular procedure such as a pullback operation.

In an embodiment, intravascular instrument 402 may comprise elements of the system 150 and/or may interact with elements of the system 150. In that regard, in some instances, intravascular instrument 402 may be suitable for use as at least one of instruments 130, 132, 152, 175, or 202 discussed above. Accordingly, in some instances the intravascular instrument 402 includes features similar to those discussed above with respect to one or more of instruments 130, 132, 152, 175, or 202. In some cases, the intravascular instrument 402 may comprise a pressure-sensing guide wire or catheter. In some cases, the intravascular instrument 402 may comprise an IVUS guide wire or catheter.

Intravascular instrument 402 may comprise one or more radiopaque regions 414 and one or more non-radiopaque regions 416. The particular pattern formed by the radiopaque regions 414 and non-radiopaque regions 416 may permit a medical processing unit, e.g., computing device 172, to detect and/or track the intravascular instrument 402 within radiographic images. For example, the medical processing unit may analyze radiographic imaging data received from a radiographic imaging unit, e.g., radiographic imaging unit 186, in search of a characteristic pattern by which the intravascular instrument 402 may be identified. In that regard, tracking the intravascular instrument 402 may comprise tracking the radiopaque regions 414 and/or tracking the pattern. The intravascular instrument 402 may be tracked continuously, every millisecond, every hundredth of a second, every tenth of a second, every 0.25 seconds, every second, may be tracked over some other timeframe, may be tracked in response to a trigger such as a heartbeat or data acquisition event, or may be tracked under any combination of the foregoing. The radiopaque region 414 can be a radiopaque marker or the sensor of the instrument 402. In some instances, the processor can be configured to distinguish between the radiopaque marker and the sensor such that the location of the sensor is identified to locate where in the vessel the intravascular data is obtained at a given time or frame of radiographic image stream. In some instances, the processor uses the radiopaque marker pattern or known arrangement of the radiopaque marker and the sensor to identify the location of the sensor in the vessel.

In some cases, the pattern formed by the radiopaque regions 414 and non-radiopaque regions 416 may further allow the medical processing unit to determine the location of a data acquisition element of the intravascular instrument 402, e.g., a pressure sensor, ultrasound transducer or transducer array, etc. The location of the data acquisition element may be used in co-registering intravascular data with a radiographic image, e.g., an angiographic image. As used herein, co-registration of intravascular data with a radiographic image refers to displaying intravascular data adjacent to and/or overlaid on the radiographic image along with an indication of a location on the radiographic image representative of where the intravascular data was obtained within the vasculature.

The processor can co-register the location of the instrument 402, such as the data acquisition element, in each frame of radiographic data that is obtained. In this manner, the processor identifies the location of the instrument 402 within the vessel for each radiographic image frame. The processor determines the location of the instrument 402 with co-registration and receives the time at which the respective radiographic image frame was obtained from the radiographic image source. The processor calculates the movement speed of the intravascular instrument using locations of the instrument 402 and the corresponding image time stamps. Aspects of co-registration are described, for example, in U.S. Pat. Nos. 7,930,014 and 8,298,147, the entireties of which are hereby incorporated by reference.

The medical processing unit may calculate a movement speed of the intravascular instrument 402 as it moves through the vasculature. The movement speed may be calculated based on tracking the intravascular instrument 402. For example, by tracking the intravascular instrument 402, the medical processing unit may be able to determine how far the intravascular instrument has moved over a certain period of time. If the intravascular instrument has moved 2 millimeters in one second, then the movement speed of the intravascular instrument 402 is 2 millimeters per second. The medical processing unit may calculate the movement speed continuously, every millisecond, every hundredth of a second, every tenth of a second, every 0.25 seconds, every second, may calculate the movement speed after some other elapse of time, may calculate the movement speed in response to a trigger such as a heartbeat or data acquisition event, or may calculate the movement speed in response to any combination of the foregoing. In some instances, the medical processing unit may calculate the movement speed for every frame of radiographic imaging data (e.g., 30 frames per second or other suitable amount). The calculated movement speed may reflect a current speed, an average speed, a mode speed, or any combination of the foregoing. The speed of the intravascular instrument 402 may be the speed of the sensor in some embodiments.

As discussed above, calculation of the movement speed may be based on tracking the intravascular instrument 402 in a radiographic image or multiple radiographic images from an image stream. Generally, movement of the intravascular instrument 402 in the radiographic image is representative of movement of the intravascular instrument 402 in the vasculature. It should be understood, however, that in some cases the radiographic images are two dimensional. In such cases, the radiographic images may depict movement in the X and Y planes while failing to depict movement in the Z plane. The intravascular instrument 402 may travel through three dimensional vasculature and may move in X, Y, and Z planes. To account for movement in the Z plane, the medical processing unit may access conversion data, e.g., anatomical data, as discussed below. In other cases, e.g., in biplane angiography, three dimensional radiographic images may be obtained which allow the intravascular instrument 402 to be tracked in the X, Y, and Z planes within the radiographic image itself. It should also be understood that the radiographic image may be magnified by some factor such that, even with respect to movement purely in the X and Y planes, movement of a certain distance in the radiographic image does not equate to movement of the same distance within the vasculature. As discussed below, the medical processing unit may access conversion data, e.g., scaling data, to account for such magnification.

The medical processing unit may store, either locally or remotely, conversion data to allow the medical processing unit to extrapolate movement within the vasculature from movement in the radiographic image. Conversion data may include scaling data, e.g., data indicating by what factor the radiographic image magnifies the vasculature. Conversion data may also include anatomical data, e.g., data regarding the three dimensional structure of the vasculature. Such anatomical data may be based on medical averages and/or may be based on patient-specific anatomical data. Anatomical data may be determined by the medical processing unit based on past procedures and may be updated as new procedures are performed. Accordingly, calculating the movement speed may comprise compensating for motion in a Z plane and/or compensating for a magnification factor.

In some cases, calculation of the movement speed also takes into account anatomical motion, as described, for example, in U.S. Publication No. 2010/0157041 and U.S. Pat. No. 9,216,065, the entireties of which are hereby incorporated by reference. Anatomical motion may include a patient's heartbeat, inflation and deflation of a patient's lungs, contraction or relaxation of one or more muscles, etc. Movement due to anatomical motion may be canceled out so as not to skew calculation of the movement speed of the intravascular instrument 402 through the vasculature. In that regard, the medical processing unit may store, either locally or remotely, anatomical motion data that identifies characteristics of various anatomical motions. The medical processing unit may identify and cancel out anatomical motion based on the anatomical motion data.

The calculated movement speed may be displayed on display 400, as shown in FIGS. 7A-7C. Though the movement speed is displayed adjacent to the radiographic images in FIGS. 7A-7C, it should be understood that the movement speed may in some instances be overlaid on the radiographic images and in some cases may be overlaid proximate to or adjacent to the intravascular instrument 402 or a data acquisition element of the intravascular instrument 402. The calculated movement speed displayed on display 400 may reflect a current speed, as shown in FIGS. 7A-7C, an average speed, a mode speed, or any combination thereof.

The medical processing unit may compare the calculated movement speed to a predefined target movement speed. The medical processing unit may then provide guidance to a user, e.g., a physician or operator, based on the comparison. For example, the medical processing unit may output guidance in the form of a speed-adjustment suggestion to the display 400. Speed-adjustment suggestions may include suggestions to speed up, slow down, maintain speed (as shown in FIGS. 7A-7C), suggestions to repeat an intravascular procedure, e.g., a pullback operation, or any combination thereof. A suggestion to speed up may be made when the calculated movement speed is below the target movement speed. A suggestion to slow down may be made when the calculated movement speed is above the target movement speed. A suggestion to maintain speed may be made when the calculated movement speed matches the target movement speed. A suggestion to repeat an intravascular procedure may be made when the data quality is below a predefined threshold, when an average speed over the duration of an intravascular procedure or for some portion of the intravascular procedure is above or below a predefined threshold, when co-registration accuracy falls below a predefined threshold, or any combination thereof. The medical processing unit may output speed-adjustment suggestions continuously, every millisecond, every hundredth of a second, every tenth of a second, every 0.25 seconds, every second, after some other elapse of time, in response to a trigger such as a heartbeat, data acquisition event, or completion of a comparison between the calculated movement speed and the target movement speed, or may output speed-adjustment suggestions in response to any combination of the foregoing.

Such speed-adjustment suggestions advantageously increase the likelihood that the intravascular instrument will be moved at a suitable speed for intravascular data acquisition and co-registration of said intravascular data with the radiographic images. Accordingly, such guidance also advantageously improves efficiency by reducing the likelihood that an intravascular procedure will be repeated on account of poor data and/or inaccurate co-registration. In the event that intravascular data acquisition and/or co-registration were unsuccessful, such guidance advantageously helps to ensure that the intravascular procedure is repeated when appropriate.

Guidance may be outputted in the form of graphics, text, symbols, sounds, tactile feedback, or any combination thereof. For example, FIGS. 8A-8D show diagrammatic, schematic views of a display 500 depicting speed-adjustment suggestions. In that regard, FIGS. 8A and 8B show two different graphics 525, an upward arrow and a rabbit, respectively, suggesting that a user increase the speed at which an intravascular instrument is moved through the vasculature. The graphics 525 are accompanied by text 535 advising the user to "Speed Up!" in FIGS. 8A and 8B. FIGS. 8C and 8D show two different graphics 525, a downward arrow and a turtle, respectively, suggesting that the user decrease the speed at which the intravascular instrument is moved through the vasculature. The graphics 525 are accompanied by text 535 advising the user to "Slow Down!" in FIGS. 8C and 8D.

In cases where movement of the intravascular instrument is automatically controlled, the medical processing unit may or may not output guidance to a display. In that regard, the medical processing unit may automatically adjust the speed of the intravascular instrument, e.g., by automatically adjusting the speed of a pullback device, based on a comparison of the calculated movement speed with the target movement speed.

Figure 9A:
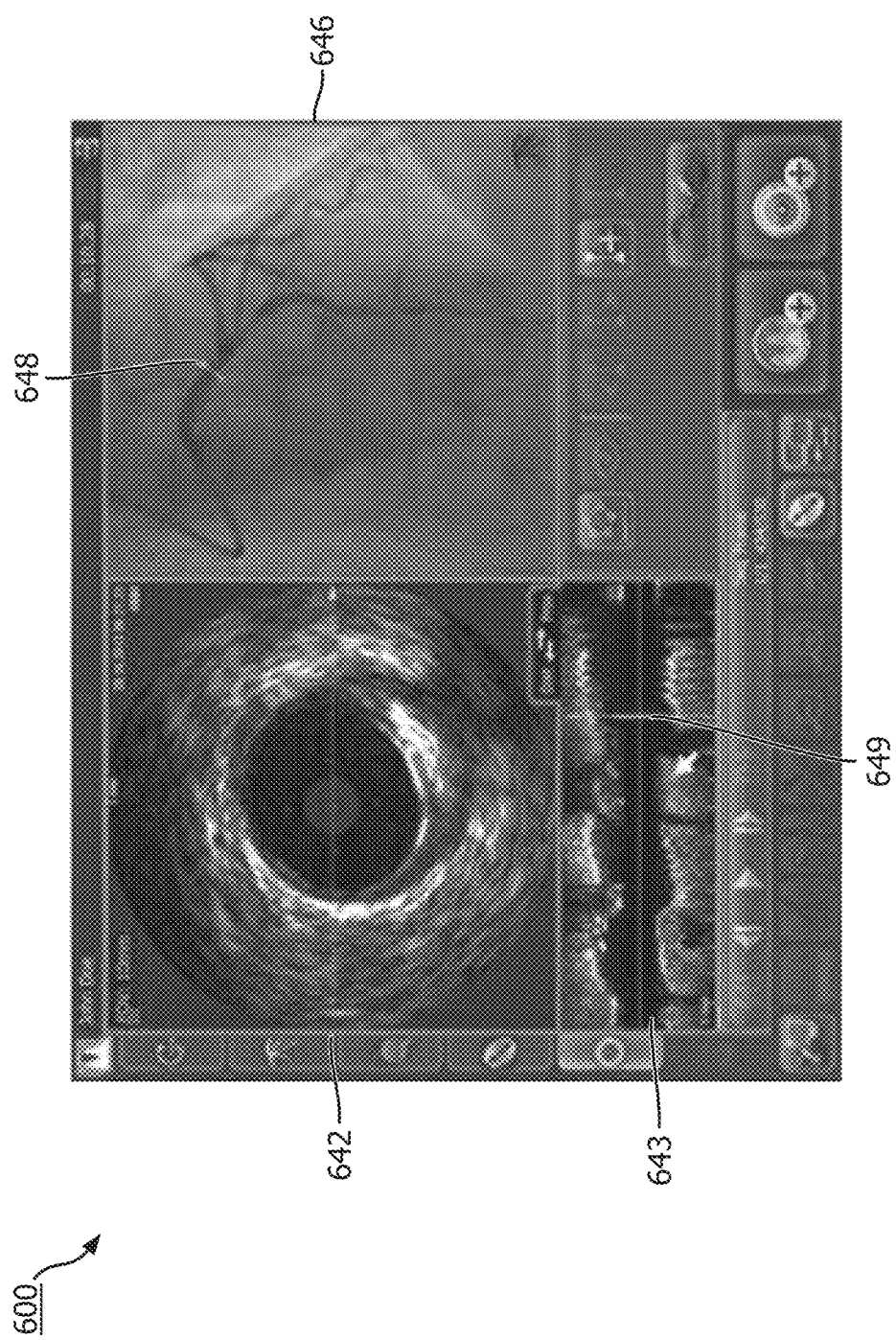
FIG. 9A is an image of a display showing co-registration of intravascular data with a radiographic image according to an embodiment of the present disclosure.

Turning now to FIG. 9A, shown therein is a illustration of a screen display 600 depicting co-registration of intravascular data 642 with a radiographic image 646. In FIG. 9A, intravascular data 642 comprises a tomographic IVUS image. Intravascular data 643 comprises a longitudinal view of the vessel comprising a stack of tomographic IVUS images. The radiographic image 646 comprises an angiographic image in FIG. 9A. An angiographic image is useful in co-registration because the presence of contrast within the vasculature allows for better viewing of the location of the various vessels making up the vasculature. A location marker 648 has been overlaid on the radiographic image 646. The location marker 648 is representative of the location at which the intravascular data 642, in this case the IVUS image, was obtained. A location marker 649 is also provided in longitudinal display 643 to identify the location of the corresponding IVUS image. The IVUS data is provided in a co-registered manner as a result of the sufficient IVUS data being collected during movement of the intravascular instrument through the vessel with the proper speed. The guidance described herein can advantageously allow user to move the intravascular instrument with the proper speed.

Figure 9B:
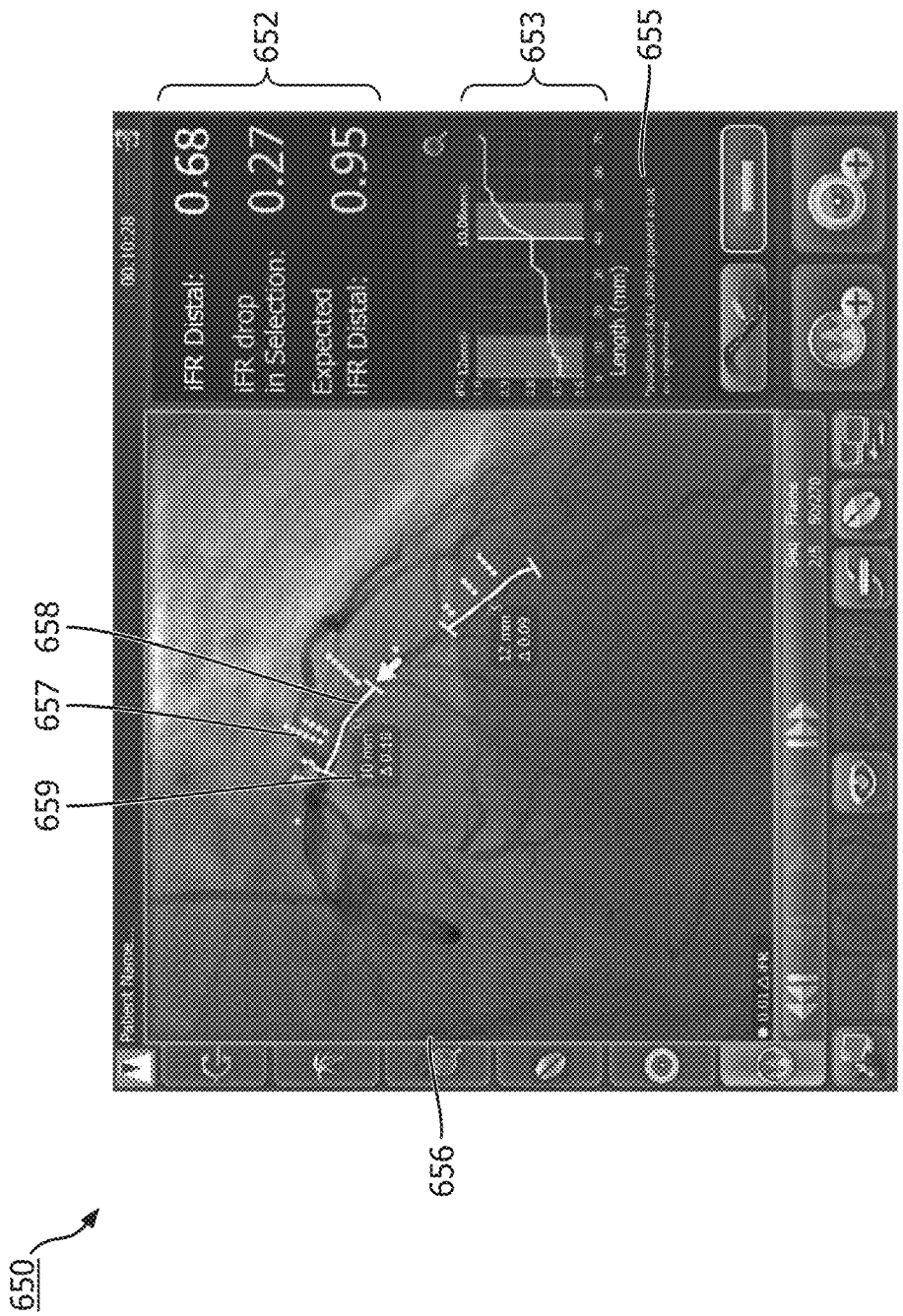
FIG. 9B is an image of a display showing co-registration of intravascular data with a radiographic image according to an embodiment of the present disclosure.

Turning now to FIG. 9B, shown therein is a diagrammatic, schematic view of a display 650 depicting co-registration of intravascular data with a radiographic image 656. In FIG. 9B, intravascular data comprises iFR values calculated from pressure measurements obtained one or more pressure sensing instruments. The radiographic image 656 comprises an angiographic image in FIG. 9B. An angiographic image is useful in co-registration because the presence of contrast within the vasculature allows for better viewing of the location of the various vessels making up the vasculature. The markers 657 are representative of a pressure drop (e.g., a change in iFR value) attributable to the adjacent location of a vessel. The marker 658 indicates a longitudinal extent of the vessel selected by the user. The overlay 659 provides the length of the vessel in selected region (marker 658) and the change in iFR value in the selected length. Numerical values 652 provide the iFR value at the distal location of the vessel (iFR Distal), the total change in IFR value in the two selected regions (iFR drop in Selection), and the expected iFR value at the distal location as a result of therapy (e.g., stent placement) in the two selected regions (Expected iFR Distal). A graph 653 of the iFR values along the length of the vessel is also provided. The iFR data is provided in a co-registered manner as a result of the sufficient pressure data being collected during movement of the intravascular instrument through the vessel with the proper speed. The guidance described herein can advantageously allow user to move the intravascular instrument with the proper speed. An indication 655 can be provided if the insufficient intravascular data has been obtained in a given segment of the vessel as a result of, e.g., the pressure sensing guidewire being moved through the vessel too quickly.

Figure 10:
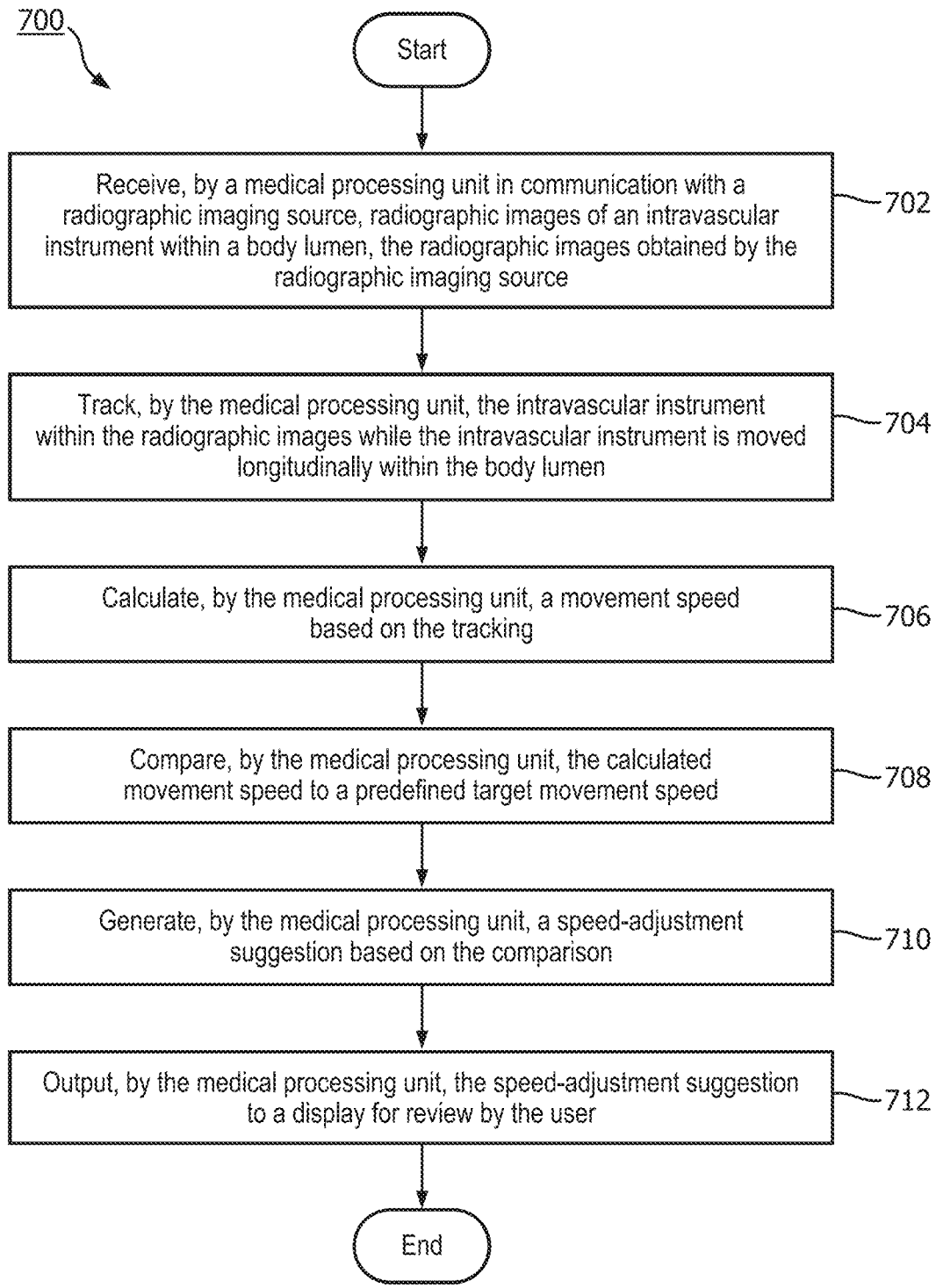
FIG. 10 is a flowchart of a method according to an embodiment of the present disclosure.

Referring now to FIG. 10, shown therein is a flow chart of a method 700 according to embodiments of the disclosure. Portions of the method 700 may correspond to techniques discussed hereinabove with reference to FIGS. 1-9B and may be performed with hardware and/or software components of the system 150, the intravascular instrument 202, the intravascular instrument 402, radiographic imaging unit 186, computing device 172, or combinations thereof. The method 700 begins at block 702 where radiographic images of an intravascular instrument within a body lumen are received by a medical processing unit in communication with a radiographic imaging source. The intravascular instrument may comprise an intravascular ultrasound (IVUS) guidewire or catheter. The intravascular instrument may comprise a pressure sensing guidewire or catheter. The radiographic images may be obtained by the radiographic imaging source. The method continues at block 704 where the medical processing unit tracks the intravascular instrument within the radiographic images while the intravascular instrument is moved longitudinally within the body lumen. Block 704 can include co-registration such that the location of the intravascular instrument is identified in radiographic image frames as the intravascular instrument is moved within the body lumen. The medical processing unit calculates, at block 706, a movement speed of the intravascular instrument based on the tracking. Calculating the movement speed may comprise compensating for motion of a heartbeat. The medical processing unit compares the calculated movement speed to a predefined target movement speed at block 708. The predefined target movement speed may comprise a target range between 1 and 3 millimeters per second, inclusive. The method continues at block 710 where the medical processing unit generates a speed-adjustment suggestion based on the comparison. The medical processing unit outputs, at block 712, the speed-adjustment suggestion to a display for review by a user. The speed-adjustment suggestion may comprise a graphic image configured to instruct the user to increase, decrease, or maintain the speed at which the intravascular instrument is moved within the body lumen. The speed-adjustment suggestion may comprise textual instructions to increase, decrease, or maintain the speed at which the intravascular instrument is moved within the body lumen. The speed-adjustment suggestion may comprise a suggestion to repeat a pullback operation. Though not shown in FIG. 10, the method 700 may further comprise additional steps consistent with the foregoing disclosure. Further, the method 700 may omit some of the steps shown in FIG. 10 and/or perform the steps in various orders without departing from the scope of the present disclosure.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A medical system, comprising:
a processor configured for communication with:
an intravascular instrument configured to be moved longitudinally within a body lumen; and
a radiographic imaging source configured to obtain radiographic images of the intravascular instrument while the intravascular instrument is moved longitudinally within the body lumen,
wherein the processor is configured to:
receive radiographic images obtained by the radiographic imaging source;
track the intravascular instrument within the radiographic images while the intravascular instrument is moved longitudinally within the body lumen;
calculate a movement speed based on the tracking;
compare the calculated movement speed to a predefined target movement speed;
generate a speed-adjustment suggestion based on the comparison; and
output the speed-adjustment suggestion to a display for review by a user.

2. The medical system of claim 1, wherein the predefined target movement speed is between 1 and 3 millimeters per second, inclusive.

3. The medical system of claim 1, wherein calculating the movement speed comprises compensating for motion of a heartbeat.

4. The medical system of claim 1, wherein the intravascular instrument comprises an intravascular ultrasound (IVUS) catheter.

5. The medical system of claim 1, wherein the intravascular instrument comprises a pressure sensing guidewire.

6. The medical system of claim 1, wherein the intravascular instrument comprises a radiopaque marker, and wherein tracking the intravascular instrument within the radiographic images comprises tracking the radiopaque marker within the radiographic images.

7. The medical system of claim 1, wherein if the calculated movement speed is below the target movement speed, then the speed-adjustment suggestion comprises a suggestion to increase the speed at which the intravascular instrument is moved within the body lumen.

8. The medical system of claim 1, wherein if the calculated movement speed is above the target movement speed, then the speed-adjustment suggestion comprises a suggestion to decrease the speed at which the intravascular instrument is moved within the body lumen.

9. The medical system of claim 1, wherein if the calculated movement speed matches the target movement speed, then the speed-adjustment suggestion comprises a suggestion to maintain the speed at which the intravascular instrument is moved within the body lumen.

10. The medical system of claim 1, wherein calculating the movement speed comprises accounting for movement of the intravascular instrument through the body lumen in a Z-plane.

11. The medical system of claim 10, wherein accounting for movement of the intravascular instrument through the body lumen in a Z-plane is based on an analysis of radiographic images obtained during biplane angiography.

12. The medical system of claim 10, wherein accounting for movement of the intravascular instrument through the body lumen in a Z-plane is based on an analysis of anatomical data relating to the structure of the body lumen.

13. A method, comprising:
  receiving, by a processor in communication with a radiographic imaging source, radiographic images of an intravascular instrument within a body lumen, the radiographic images obtained by the radiographic imaging source;
  tracking, by the processor, the intravascular instrument within the radiographic images while the intravascular instrument is moved longitudinally within the body lumen;
  calculating, by the processor, a movement speed based on the tracking;
  comparing, by the processor, the calculated movement speed to a predefined target movement speed;
  generating, by the processor, a speed-adjustment suggestion based on the comparison; and
  outputting, by the processor, the speed-adjustment suggestion to a display for review by a user.

14. The method of claim 13, wherein the predefined target movement speed comprises a target range between 1 and 3 millimeters per second, inclusive.

15. The method of claim 13, wherein the speed-adjustment suggestion comprises a graphic image configured to instruct the user to increase, decrease, or maintain the speed at which the intravascular instrument is moved within the body lumen.

16. The method of claim 13, wherein the speed-adjustment suggestion comprises textual instructions to increase, decrease, or maintain the speed at which the intravascular instrument is moved within the body lumen.

17. The method of claim 13, wherein the speed-adjustment suggestion comprises a suggestion to repeat a pullback operation.

18. The method of claim 13, wherein the intravascular instrument comprises an intravascular ultrasound (IVUS) catheter.

19. The method of claim 13, wherein the intravascular instrument comprises a pressure sensing guidewire.

20. The method of claim 13, wherein calculating the movement speed comprises compensating for motion of a heartbeat.

* * * * *